US00RE42034E

(19) United States
(12) Reissued Patent
Cho et al.

(10) Patent Number: US RE42,034 E
(45) Date of Reissued Patent: Jan. 18, 2011

(54) METHOD AND APPARATUS FOR ULTRA FAST SYMMETRY AND SIMD BASED PROJECTION-BACK PROJECTION FOR 3D PET IMAGE RECONSTRUCTION

(75) Inventors: Zang Hee Cho, Incheon (KR); Young Bo Kim, Seongnam-si (KR); Cheol Ok Lee, Incheon (KR); In Ki Hong, Miseong Apt. 7-107, Sincheon-dong, Songpa-gu, Seoul 138-240 (KR); Sung Tak Chung, Yongin-si (KR); Hang Keun Kim, Seoul (KR); Young Don Son, Incheon (KR)

(73) Assignees: Gachon University of Medicine and Science Industry-Academic Cooperation Foundation, Seoul (KR); In Ki Hong, Seoul (KR)

(21) Appl. No.: 12/498,952

(22) Filed: Jul. 7, 2009

Related U.S. Patent Documents

Reissue of:
(64) Patent No.: 7,456,406
Issued: Nov. 25, 2008
Appl. No.: 11/800,657
Filed: May 7, 2007

(30) Foreign Application Priority Data

May 10, 2006 (KR) ..... 10-2006-0042155
Mar. 20, 2007 (KR) ..... 10-2007-0027305
Apr. 25, 2007 (KR) ..... 10-2007-0040515

(51) Int. Cl.
*G01T 1/166* (2006.01)

(52) U.S. Cl. ..... 250/363.04
(58) Field of Classification Search .. 250/363.01–363.1; 370/210; 378/98.8
See application file for complete search history.

(56) References Cited

U.S. PATENT DOCUMENTS 6,282,257 B1 * 8/2001 Basu et al. ..... 378/15
7,522,695 B2 * 4/2009 Nishide et al. ..... 378/4
2002/0054659 A1 * 5/2002 Okumura et al. ..... 378/19
2002/0106051 A1 8/2002 Menhardt
2002/0122528 A1 9/2002 Besson
2002/0154727 A1 10/2002 Ning
2003/0161443 A1 * 8/2003 Xiao et al. ..... 378/210
2005/0123089 A1 6/2005 Man

OTHER PUBLICATIONS

Official Korean Action, with Translation, dated Sep. 18, 2008, as cited in Korean Patent Application No. 10–2007–0040515. 8 Pgs.

I.K. Hong, et al., "Fast Forward Projection and Backward Projection Algorithm Using SIMD," *IEEE, San Francisco 2006, Conference Program,* M14–372.

* cited by examiner

*Primary Examiner*—David P Porta
*Assistant Examiner*—Kiho Kim
(74) *Attorney, Agent, or Firm*—Patterson Thuente Christensen Pedersn, P.A.

(57) ABSTRACT

A method and apparatus are provided for reconstructing 3D image. The method may include the steps of: detecting a plurality of line of response (LORs) emitted from an object; transforming the plurality of LORs into first sinogram data; back-projecting the first sinogram data with a plurality of projection angles to produce image data for the object; and projecting the produced image data with the plurality of projection angles to transform the image data into second sinogram data. The back-projecting may include filling pixels of image plane for each of the plurality of projection angles with the first sinogram data and rotating a coordinate axis of the image plane with corresponding projection angle to produce the image data. The projecting may include rotating the image data with corresponding projection angle in an opposite direction before projecting the image data with the plurality of projection angles. The projecting and the back-projecting may use symmetry properties in coordinate space.

21 Claims, 20 Drawing Sheets

----> Ray Path $\vec{T}_{x_r, y_r, \Phi, \theta}$

| |
|---|
| $x_r = x' = x \cos\Phi + y \sin\Phi$ |
| $y_r = z - y' \tan\theta$<br>$= z - (-x \cos\Phi + y \sin\Phi) \tan\theta$ |

By Existing Method

By the proposed SSP Method

Differences

By Existing Method

By the proposed SSP Method

Differences

METHOD AND APPARATUS FOR ULTRA FAST SYMMETRY AND SIMD BASED PROJECTION-BACK PROJECTION FOR 3D PET IMAGE RECONSTRUCTION

Matter enclosed in heavy brackets [ ] appears in the original patent but forms no part of this reissue specification; matter printed in italics indicates the additions made by reissue.

The present application claims priority from Korean Patent Application No. 10-2006-0042155 filed on May 10, 2006, Korean Patent Application No. 10-2007-0027305 filed on Mar. 20, 2007, and Korean Patent Application No. 10-2007-0040515 filed on Apr. 25, 2007, the entire subject matter of which is incorporated herein by reference.

BACKGROUND

1. Field

The present invention relates to a method and apparatus for ultra fast symmetry and SIMD based projection-backprojection for 3D PET image reconstruction. More specifically, the present invention relates to a method and apparatus based on the symmetry properties of the projection and backprojection processes, especially in the 3D OSEM algorithm that requires a plurality of projections and back-projections.

2. Background

There has been a remarkable progress in PET development over the recent years, especially in the areas of hardware, software and computer implementation of image reconstruction. Recent developments in PET scanners (e.g., HRRT (High Resolution Research Tomograph) developed by CTI (now Siemens)) allow greatly enhanced resolution and sensitivity. In such PET scanners, the amount of collected coincidence line data contains more than $4.5\times10^9$ coincidence lines of response generated by as many as 120,000 nuclear detectors. Such large amount of data and the reconstruction of this data set pose to be a real problem in HRRT. That is, they pose to be major problems in achieving further developments and applications of high resolution PET scanners. Thus, in such types of scanners, obtaining one set of reconstructed images often requires many hours of image reconstruction. For example, in HRRT with full data collection in normal brain scans (using SPAN 3), the image reconstruction time is almost eighty minutes. This makes it practically impossible to attempt any list mode based dynamic imaging since the image reconstruction time takes many days (as long as 43 hours or more for 32 frame dynamic image reconstruction).

In general, tomographic images can be reconstructed by two approaches, one being an analytic method and the other being an iterative approach. PET scanners of different types were developed in the mid 1970's and the application of various tomographic image reconstruction techniques was naturally introduced in the field. In case of an analytic approach such as backprojection and filtering or filtered back-projection (FB), an artifact known as a streak artifact is frequently generated. This is especially true when the detector arrangements are not uniform such as in the case of HRRT (e.g., Siemens' High Resolution Research Tomograph) where the detectors are arranged in a set of blocks in an octagonal shape. These types of detector arrangements often involve missing data due to the gaps between the blocks and result in a severe streak artifact in the case of the FB technique. Therefore, alternative approaches such as an EM (Expectation Maximum) algorithm have been sought. Generally, the EM approach requires several steps in the reconstruction process, the two major steps of which are: projection (forward projection) to create projection data from the image or object and backprojection into the image domain for the final image reconstruction. In the EM algorithms, these two processes are repeated until satisfactory images are obtained. Obviously, these repeated projection and backprojection processes are time consuming and have been the major drawback of the EM approach compared to straight filtered backprojection (FB) algorithm. In addition, in case of 3D image reconstruction, the computational burden increases out of proportion due to the astronomical increases in the coincidence lines or the line of responses (LOR). This is a major stumbling block in the daily operation of high resolution PET scanners. Thus, there is a strong need for improving the computational speed or the reconstruction time in EM approaches, especially with high end PET scanners such as HRRT.

Projection methods usually employ a system matrix, which is determined by the geometric factor of the scanner. As the resolution of the PET image improves and the number of slices increases, the size of the matrix is also increased drastically in proportion to the increases in LORs, thus resulting in not only the need for a large memory but also the total computation time. Current HRRT, for example, requires nearly eighty minutes of reconstruction time, in addition to the generation of sinograms and appropriate data streaming processes such as attenuation, random and scatter corrections, a set of precursors to the reconstruction processes. To remedy the computational burden of image reconstruction, a number of alternative proposals such as linear integration have been proposed, as well as the use of multiple CPUs or a cluster computer system approach. Most of the techniques, however, are not practically useful since such cluster computing requires a large data transfer time, although the overall computation is faster than a single unit.

Obtaining or generating projection data can be divided into two categories, namely, ray-driven method and pixel-driven method. The ray-driven method calculates the linear integration directly along the ray path connecting the centers of the two opposite detector cells, whereas the pixel-driven method calculates the linear integration along the ray path centered around an image pixel for the entire projection angles. The ray-driven method is often used in projection, while pixel-driven method is used in backprojection.

In early reconstruction techniques, projection was obtained by weighing the ray passing through the areas of pixels with the assumption that the ray path is a strip with a finite width. It, however, involves a large amount of computation as well as the storage of a large number of matrix or data. Concurrently, Shepp and Logan proposed a simple and computationally efficient algorithm, which requires computing the length of the ray path intersecting with each pixel (instead of the areas).

To speed up the computation, there have been a number of attempts to reduce the reconstruction time. An incremental algorithm has also been developed in which the symmetric property between the neighboring pixels is considered to calculate the position of intersection of a ray. This idea was expanded to 3D reconstruction in cylindrical geometry using oblique rays. In 3D form with a multi-ring system such as HRRT, it became apparent that true 3D approaches will be required to fully utilize the oblique rays to thereby improve the statistics of the image.

BRIEF DESCRIPTION OF THE DRAWINGS

Arrangements and embodiments may be described in detail with reference to the following drawings in which like reference numerals refer to like elements and wherein.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Overview of the Projection, Backprojection and Symmetry Properties

Figure 1A:
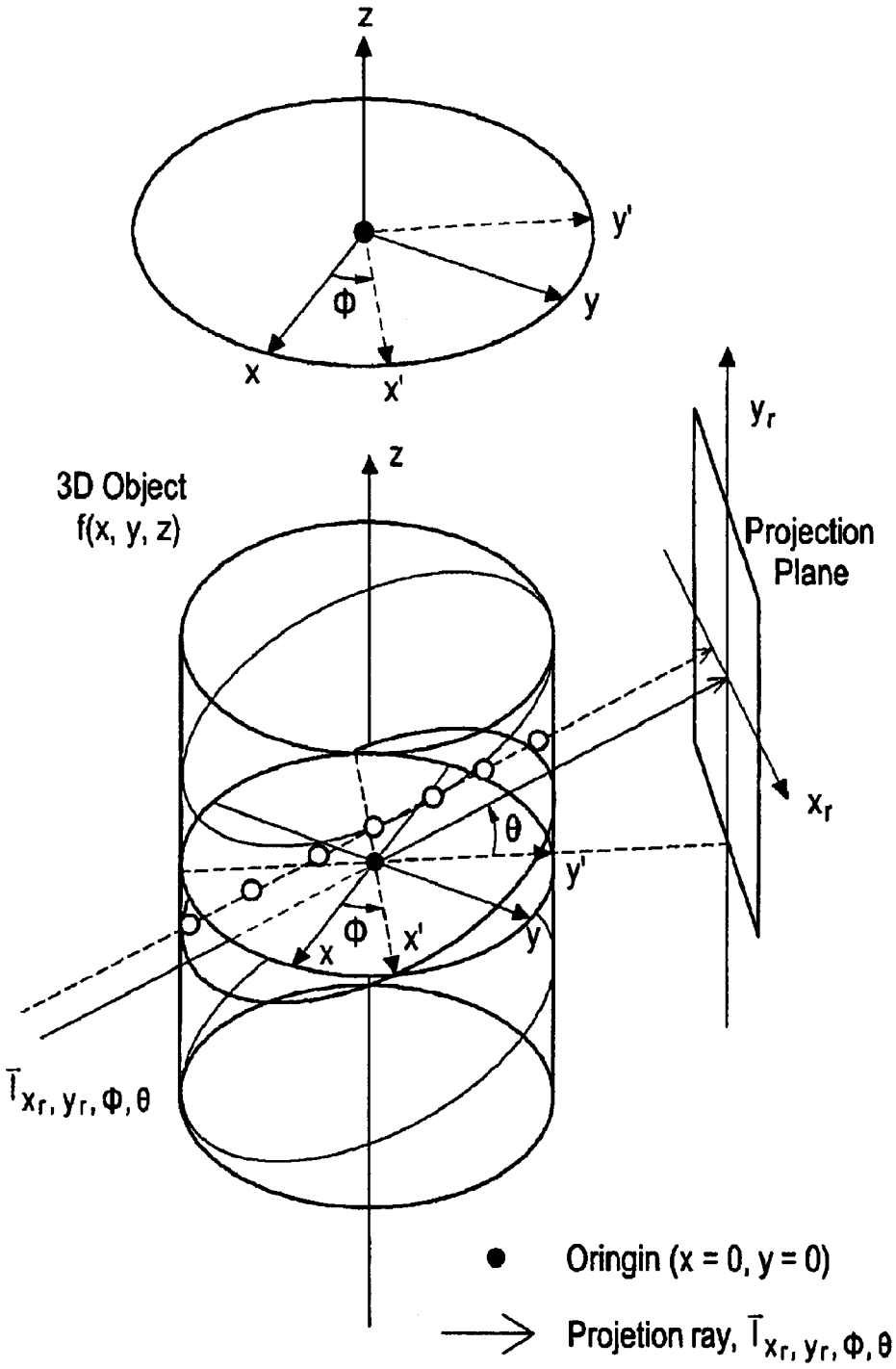
FIG. 1A illustrates a 3-D object and its projection to a 2-D projection plane.
Figure 1B:
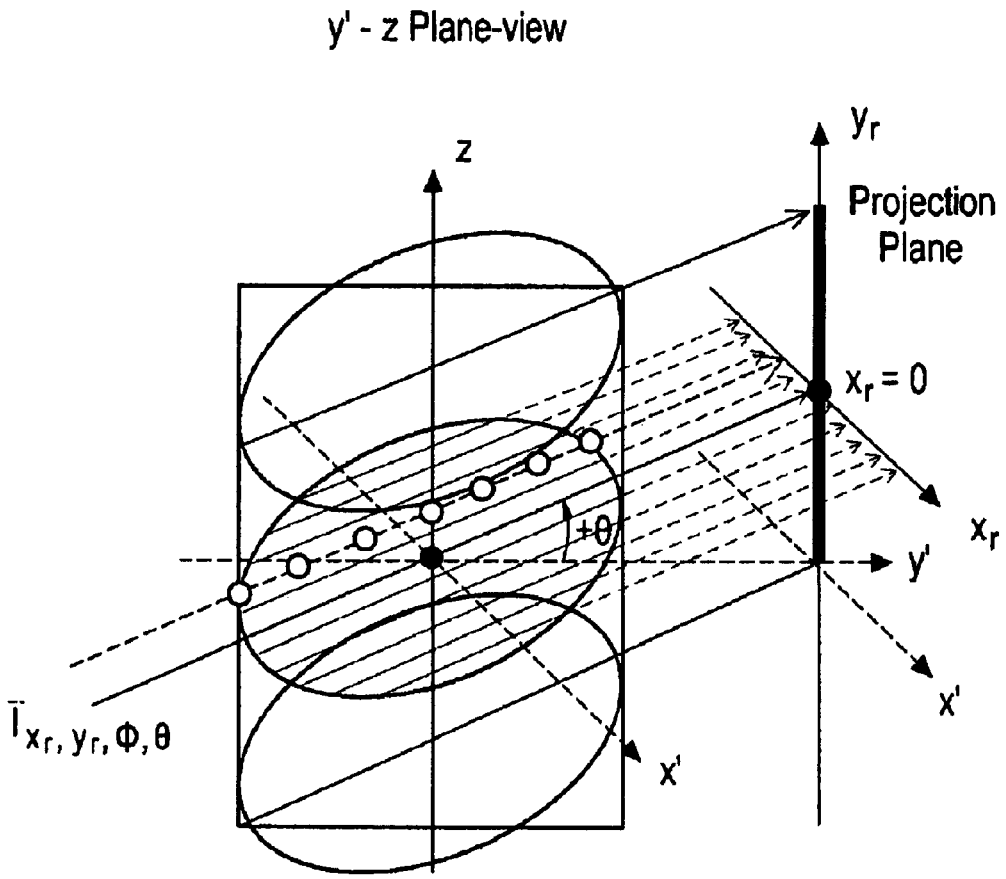
FIG. 1B illustrates a y'-z plane view of FIG. 1A.
Figure 1C:
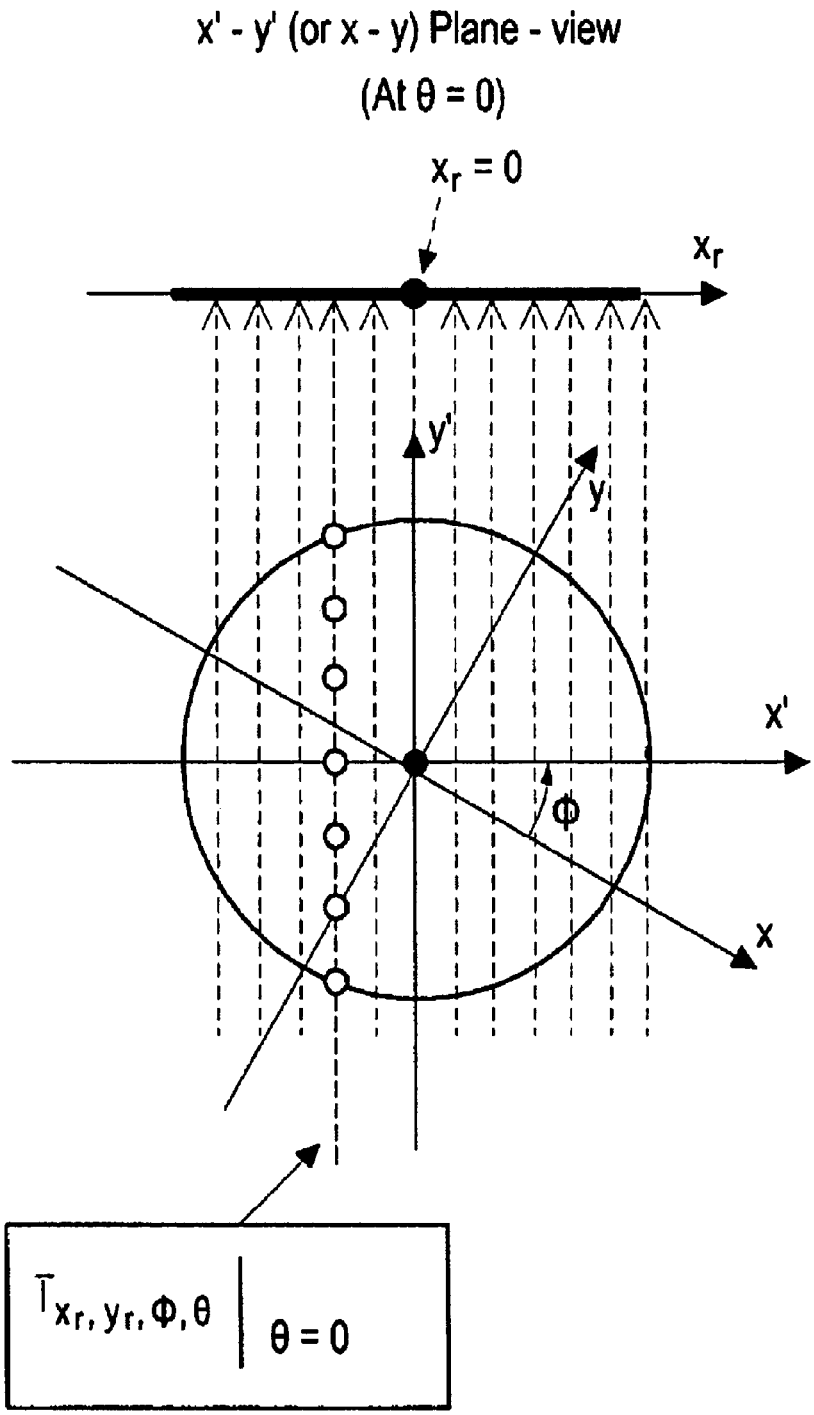
FIG. 1C illustrates an example of the transverse plane at $\theta=0°$ and the line integrals along the y' line projected on to the $x_r$.

A. Overview of Projection and Backprojection in the Aligned (Reference) Frame with Rotated Projection Plane FIG. 1A illustrates a 3-D object and its projection to a 2-D projection plane. FIG. 1B is a y'-z plane view of FIG. 1A. There is provided a relation between projection planes and the path of the projection ray, i.e., $\vec{\iota}_{x_r,y_r,\phi,\theta}$. The line integral will be performed along $\vec{\iota}_{x_r,y_r,\phi,\theta}$. The angle +θ indicates the oblique angle of the image planes toward an upper side. $x_r$ and $y_r$ are the coordinates of the 2-D projection plane of the 3-D object. FIG. 1C is an example of the transverse plane at $\theta=0°$ and the line integrals along the y' line projected on to the $x_r$. In this figure, ϕ indicates rotation of the projection ray set in reference to the coordinate axis (x,y). Dotted lines with arrow indicate the projection rays. Each projection ray is determined by four variables, i.e., $(x_r,y_r,\phi,\theta)$. The projection plane shown in FIG. 1A is composed of 2D projection data (or bed of nails) in coordinate $(x_r,y_r)$ at a given θ and ϕ.

In 3D tomographic image processing, the projection ray has 4 dimensions, namely, $x_r$, $y_r$, ϕ and θ, as shown in the FIG. 1. Projection is a process of converting a 3D object function or image information in 3D coordinates to 2D projection coordinates, and the projection plane as shown in FIG. 1.

With a fixed view angle ϕ and oblique angle θ, the projection plane is determined as shown in FIG. 1A. In this projection plane, the definition of the projection operation can be expressed in the form of linear integral given by:

$$P_{\phi,\theta}(x_r, y_r) = \int\int\int I(x, y, z)\delta(\vec{\iota}_{x_r,y_r,\phi,\theta})dx\,dy\,dz \tag{1}$$

where $\vec{\iota}_{x_r,y_r,\phi,\theta}$ is the ray path, $x_r=x'=x\cos\phi+y\sin\phi$, $y_r=z-(-x\sin\phi+y\cos\phi)\tan\theta$.

Equation (1) describes that projection $P_{\phi,\theta}(x_r,y_r)$ is a sum of the pixel values in an image function I(x,y,z) along the path of projection ray, $\vec{\iota}_{x_r,y_r,\phi,\theta}$, in the image domain. Here, δ(.) represents a sampling function.

Figure 2A:
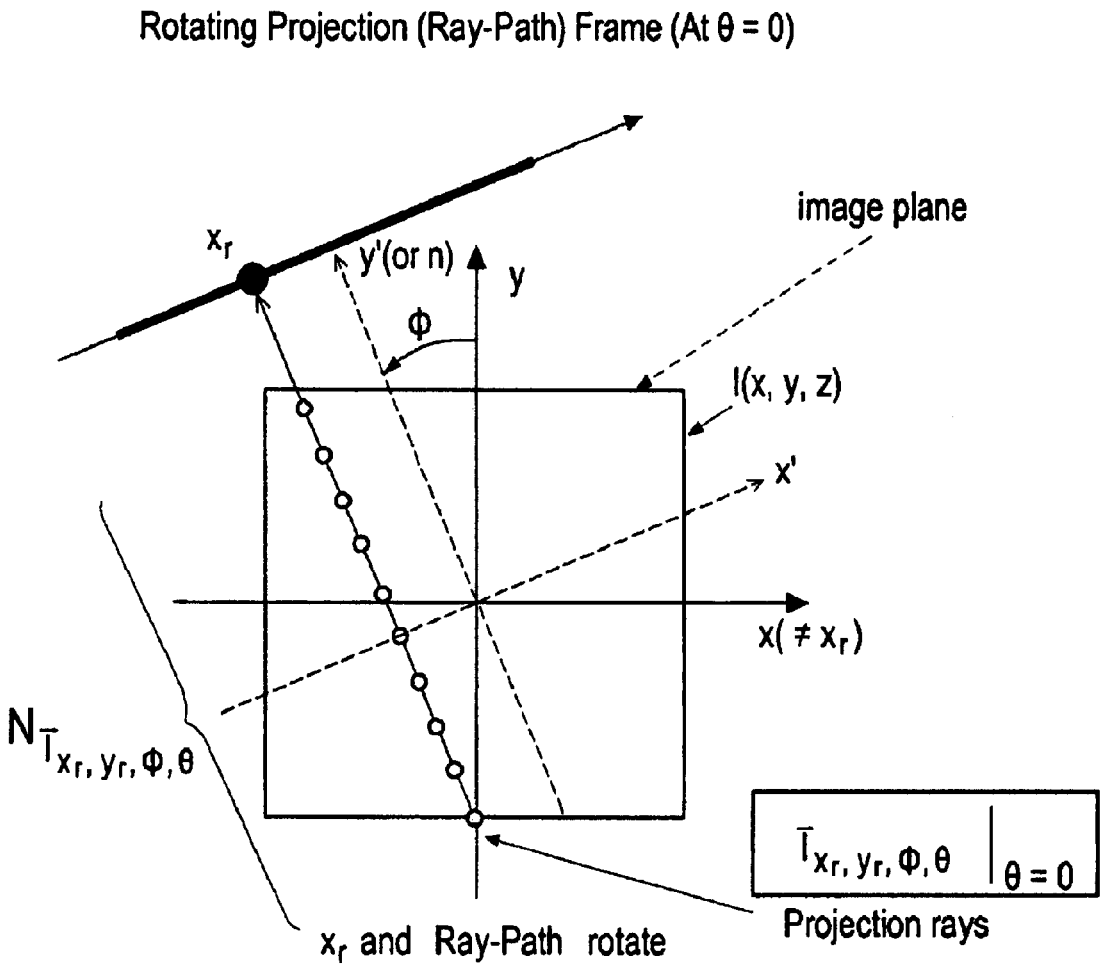
FIG. 2A illustrates a rotation of projection ray (ray-path) or frame onto the image plane which is on the fixed reference (x,y) coordinate.
Figure 2B:
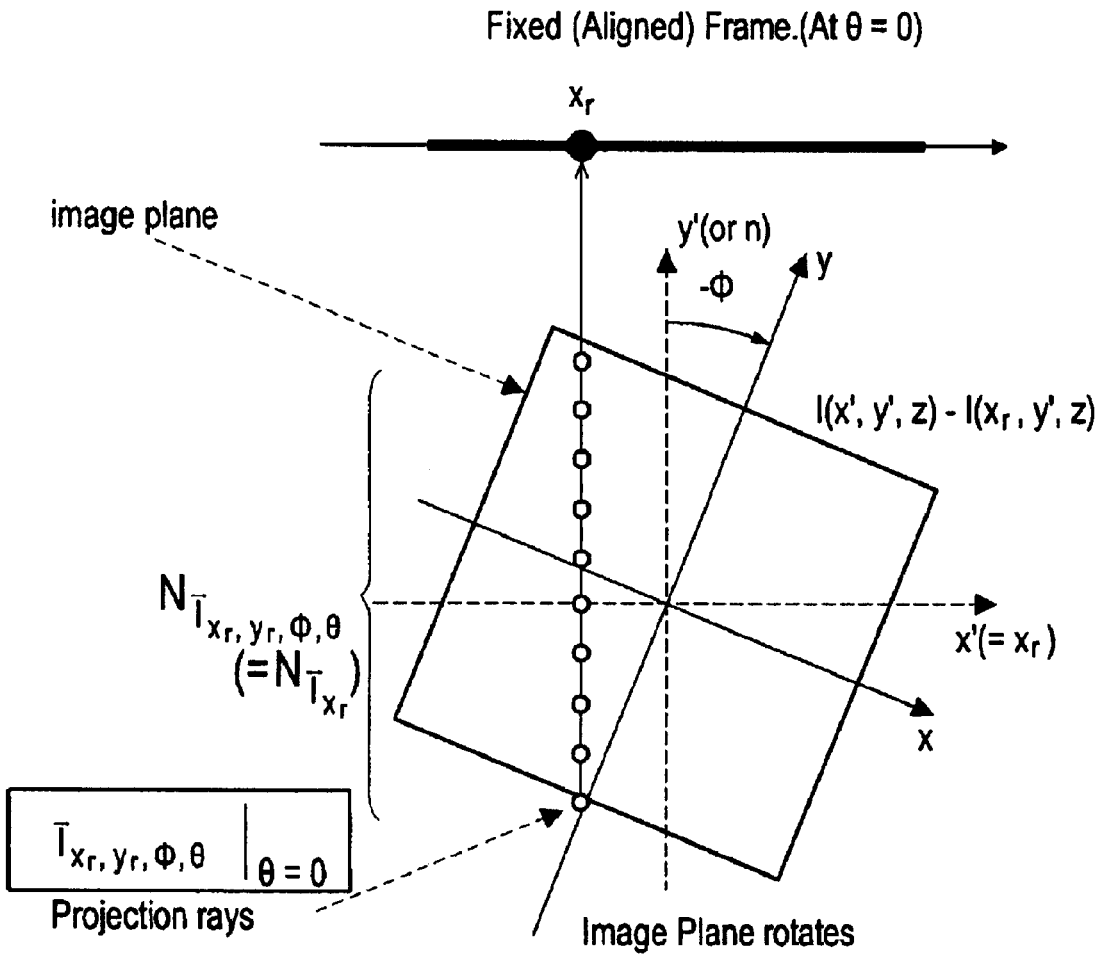
FIG. 2B illustrates the case where the projection ray (ray-path) frame coincides with the fixed (x',y') coordinate.

FIG. 2 illustrates the concepts of the rotating projection ray (ray-path) frame onto the image plane in (x,y) and the proposed fixed (aligned) projection frame with a rotating image plane. FIG. 2A illustrates the rotation of projection ray (ray-path) or frame onto the image plane, which is on the fixed reference (x,y) coordinate. This is the conventional scheme applied to most of the image reconstructions. FIG. 2B illustrates a case where the projection ray (ray-path) frame coincides with the fixed (x',y') coordinate. The latter means that the image plane is now rotated instead of the reference frame, the projection ray frame. This latter scheme is the basis of the proposed SSP (Symmetry and SIMD based Projection-backprojection) method. This scheme allows the symmetry property of the image plane to be utilized, thereby reducing the overall projection and backprojection time. In case of backprojection, the image function I (x',y',z) represents the intermediate stage of an image to be reconstructed and is a temporary image data.

It is known that a projection plane at angle θ can be rotated (or aligned) against reference axes, (x,y). Further, x' coincides with $x_r$ in FIG. 2. The well known relation between the rotated coordinate (x',y',z) and the image coordinate (x,y,z) in the cylindrical coordinate are provided by the following:

$$\begin{pmatrix} x' \\ y' \\ z \end{pmatrix} = R_\phi \cdot \begin{pmatrix} x \\ y \\ z \end{pmatrix} = \begin{pmatrix} \cos\phi & \sin\phi & 0 \\ -\sin\phi & \cos\phi & 0 \\ 0 & 0 & 1 \end{pmatrix} \begin{pmatrix} x \\ y \\ z \end{pmatrix} \tag{2}$$

where $R_\phi$ is the rotation matrix.

Equation (1) can then be simplified as the weighed sum along the ray path and can be written as follows:

$$P_{\phi,\theta}(x_r, y_r) = \int\int\int I(x, y, z)\delta(\vec{\iota}_{x_r,y_r,\phi,\theta})dx\,dy\,dz = \int I(x', y', z)dy' \quad (3)$$

where $I(x',y',z)=R_\phi I(x,y,z)$ $x'=x_r$

In (3),y' is assumed to be the integration variable.

As a special case, when the oblique angle θ is equal to zero, the projection rays are in parallel with the y' axis (see FIG. 1). In multi-layer or 3D PET, oblique rays (θ≠0) are collected and used for true 3D reconstruction since the full utilization of the oblique rays will enhance the image quality due to the increased statistics. Extension of (3) to a 3D case can be represented by θ≠0. It should be noted that the coordinates in the transverse plane are now independent of θ and the ray projected to the transverse plane is parallel to the y' axis. By the trigonometric relationship depicted in FIG. 3, z can be written as follows:

$$z=y_r+y'\tan\theta \quad (4)$$

Figure 3:
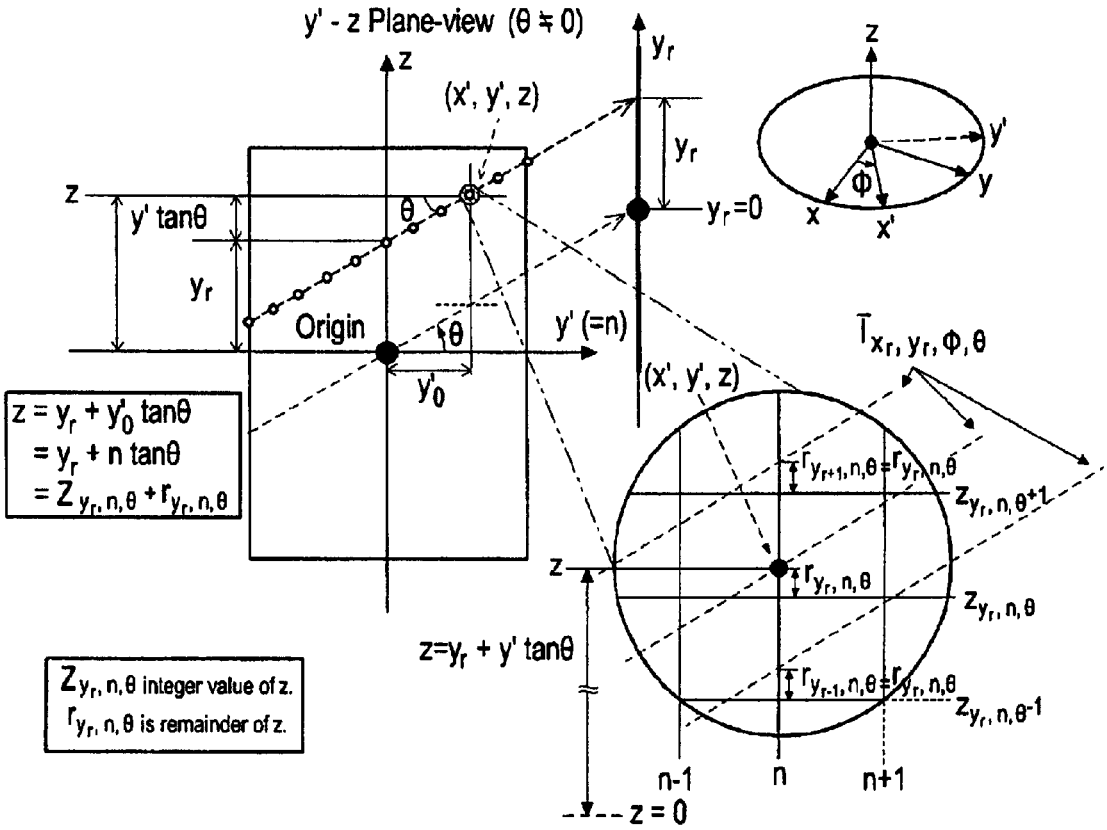
FIG. 3 illustrates the relationships among z, y', x', θ, $x_r$, $y_r$, $r_{y_r,n,\theta}$, $Z_{y_r,n,\theta}$ by using the y'-z plane view.

FIG. 3 illustrates the relationships among z, y', x', θ, $x_r$, $y_r$, $r_{y_r,n,\theta}$ and $Z_{y_r,n,\theta}$ by using the y'-z plane view. It should be noted that these relationships are valid on all the y'-z planes with any x'. Also, y' is now noted with discrete value n.

By substituting (4) into (3), the following discrete form of projection data can be obtained:

$$P_{\phi,\theta}(x_r, y_r) = \int I(x_r, y', y_r + y'\tan\theta)dy' \approx \sum_{n=-N_{I_{x_r}}/2}^{N_{I_{x_r}}/2} [I(x_r, n, y_r + n\tan\theta)] \approx \sum_{n=-N_{I_{x_r}}/2}^{N_{I_{x_r}}/2} \begin{bmatrix} I(x_r, n, Z_{y_r,n,\theta})(1 - r_{y_r,n,\theta}) + \\ I(x_r, n, Z_{y_r,n,\theta} + 1)(r_{y_r,n,\theta}) \end{bmatrix} \quad (5)$$

where $z_{y_r,n,\theta}=y_r+n\tan\theta=Z_{y_r,n,\theta}+r_{y_r,n,\theta}$ $Z_{y_r,n,\theta}\in$INTEGER, $r_{y_r,n,\theta}\in$REAL, and $0\leqq r_{y_r,n,\theta}<1$.

$Z_{y_r,n,\theta}$ is integer value of $Z_{y_r,n,\theta}$ $r_{y_r,n,\theta}$ is interpolation coefficient or remainder of $Z_{y_r,n,\theta}$ $r_{y_r,n,\theta}+r_{y_r,-n,\theta}=1$ or $r_{y_r,-n,\theta}=1-r_{y_r,n,\theta}$ n is discrete value of y'

$N_{I_{x_r}}$ is integration length of y' at given y' at given $y_r$, φ, and θ.

It should be noted that since projection rays and the coordinates (x,y,z) or (x',y',z) are not always coincident. Interpolation is always required. In case of SSP implementation, a 1D linear interpolation is needed along the z axis, as shown in (5). Note that $r_{y_r,n,\theta}$ and $1-r_{y_r,n,\theta}$ are the interpolation coefficients along the g axis.

On the other hand, the backprojection process is the transpose of projection. Therefore, the same idea as in the projection (or projection data generation) process can be applied to backprojection or image data generation. In case of an iterative reconstruction such as the OS-EM algorithm, a plurality of projections and backprojections are required. That is, algorithm requires many repeated image reconstructions as well as projection data generations.

Now the backprojection from projection data, $P_{\phi,\theta}(x_r,y_r)$, can be performed, as shown by the following:

$$I(x, y, z) = \int_\phi\int_\theta P_{\phi,\theta}(x_r, y_r)d\theta d\phi = \int_\phi\int_\theta P_{\phi,\theta}(x\cos\phi + y\sin\phi, z - (-x\sin\phi + y\cos\phi)\tan\theta)d\theta d\phi \quad (6)$$

By using rotation, the matrix defined in (2), (6) can also be written as:

$$I(x, y, z) = \int_\phi\int_\theta P_{\phi,\theta}(x', z - y'\tan\theta)d\theta d\phi \quad (7)$$

In the aligned frame, $x_r$=x' is defined.

To simplify the notation, let us define $I_\phi$ as the sum of the projection planes about θ for a fixed φ as given below as an intermediate stage image before the finally reconstructed image. The computation can then be further simplified, for example, by using the symmetry property in θ, $$I_\phi(x, y, z) \equiv \int_\theta P_{\phi,\theta}(x', z - y'\tan\theta)d\theta \quad (8)$$

Using the rotation matrix given in (2) once again, (8) can be noted as follows:

$$I_\phi(x',y',z)=R_\phi I_{100}(x,y,z) \text{ or } I_\phi(x,y,z)=R_{-\phi}I_\phi(x',y',z) \quad (9)$$

Using (9), (7) can further be noted as:

$$I(x, y, z) = \int_\phi R_{-\phi}I_\phi(x', y', z)d\phi \quad (10)$$

Equation (10) is equivalent to rotating the set of partially reconstructed image planes at a given angle φ and then integrating these partially reconstructed images over all φ's to form the finally reconstructed image I(x,y,z).

B. Symmetry Properties

As discussed above, the full utilization of symmetry properties will be the central part of the proposed SSP method. Hereafter, the symmetric points represent the similar coefficients (the same value but with different polarity and/or different coordinates) that will be shared in computation without additional calculations as well as the use of identical instructions. That is, the symmetric points have the same interpolation coefficient or complementary value. The applicant found that there exists sixteen symmetric points, which are practically usable, namely "Mirror-symmetry," "φ-symmetry," "y'-symmetry" and "θ-symmetry."

Figure 4A:
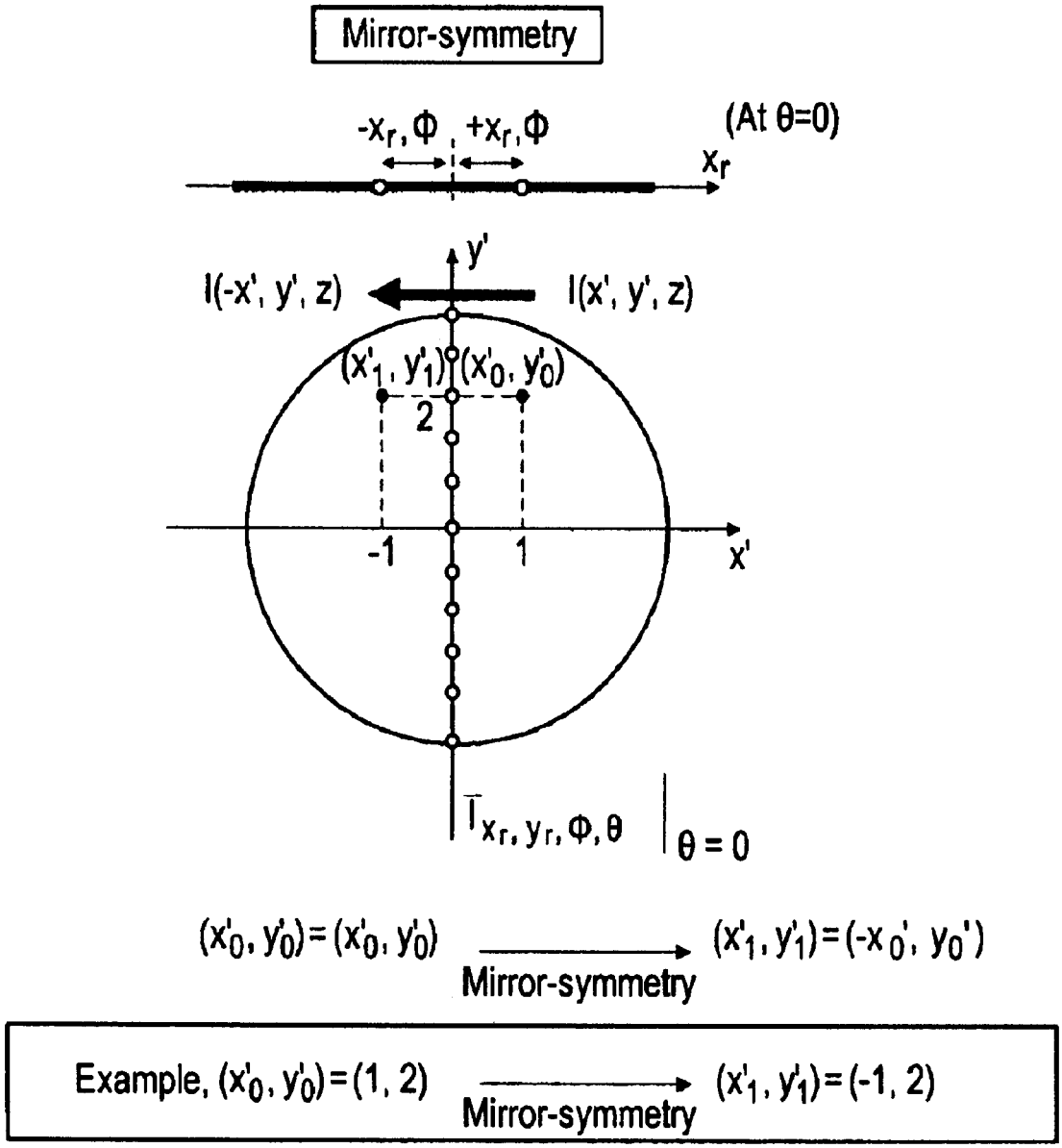
FIG. 4A illustrates an example of the "Mirror-symmetry" used in the proposed SSP method.

(a) Mirror-symmetry (+x' and −x', see FIG. 4A)

One of the interesting aspects of the image reconstruction is the use of the symmetric properties of each image point. That is, once one point is calculated with an appropriate interpolation coefficient, one can assign the same coefficient value in the opposite point(s) by using symmetry properties of various types. One of the simplest forms is the use of the y'-axis symmetry, as shown in FIG. 4A. In this computation, a point, $(x'_0,y'_0)$ at $+x_r$ is identical in value $(x'_1,y'_1)$ at $-x_r$ with change in polarity only. An illustration of this "Mirror-symmetry" is shown in FIG. 4A. In this illustration, an example is given for symmetric points due to "Mirror-symmetry", i.e., $(x'_0,y'_0)\rightarrow(x'_1,y'_1)=(-x'_0,y'_0)$. This symmetry property reduces the computation time by half.

Figure 4B:
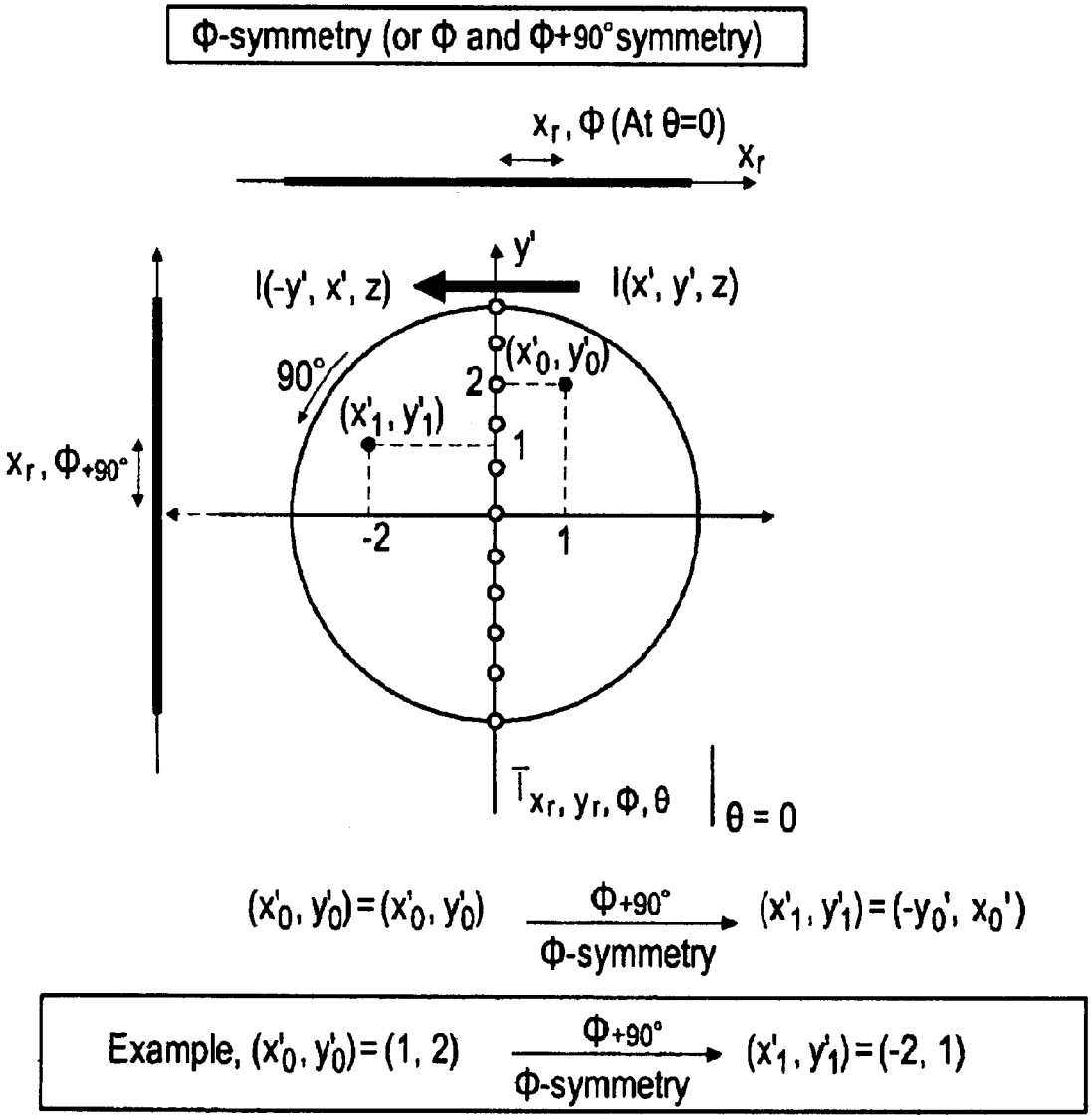
FIG. 4B illustrates an example of the "ϕ-symmetry" used in the proposed SSP method.

(b) $\phi$-symmetry ($\phi$ and $\phi+90°$ see FIG. 4B)

Similar to the case of the "Mirror-symmetry", one can also demonstrate that there is symmetry between the points at $\phi$ and $\phi+90°$ symmetry. In this case, $(x'_0,y'_0)\rightarrow(x'_1,y'_1)=(-y'_0, x'_0)$, i.e., the polarity as well as the coordinates are changed. FIG. 4B illustrates this $\phi$-symmetry case with a numerical example. As shown in the figure, once a point is calculated at $\phi$ and an interpolation coefficient value for this point is obtained, for example, at $(x'_0,y'_0)$, the same coefficient value can be used at $(x'_1,y'_1)$ with coordinate and polarity changes as $(-y'_0,x'_0)$ after a 90° rotation, i.e., at $\phi+90°$. This symmetry property once again permits the computation time to be reduced by half.

FIG. 4 illustrates the examples of the "Mirror-symmetry" and "$\phi$-symmetry" used in the proposed SSP method. FIG. 4A illustrates an example of "Mirror-symmetry" against the y' axis. That is, once a coordinate point $(x'_0,y'_0)$ is known, a symmetric point $(x'_1,y'_1)$ across the y' axis can be obtained or assigned without additional computation. This will speed up the computation by a factor of two or computation time by half. FIG. 4B illustrates the symmetric property of the projection data against 0, i.e., if an interpolation coefficient of a coordinate point $(x'_0,y'_0)$ is known at $\phi$, then a symmetric point $(x'_1,y'_0)$ at $\phi+90°$ can be obtained without additional computation. In other words, the projection data calculation at $\phi+90°$ share the same coordinate values at $\phi$ with simple coordinate changes, i.e., (x',y') at $\phi$ to (−y',x') at $\phi+90°$. This symmetry property reduces the computation time by half.

Figure 5A:
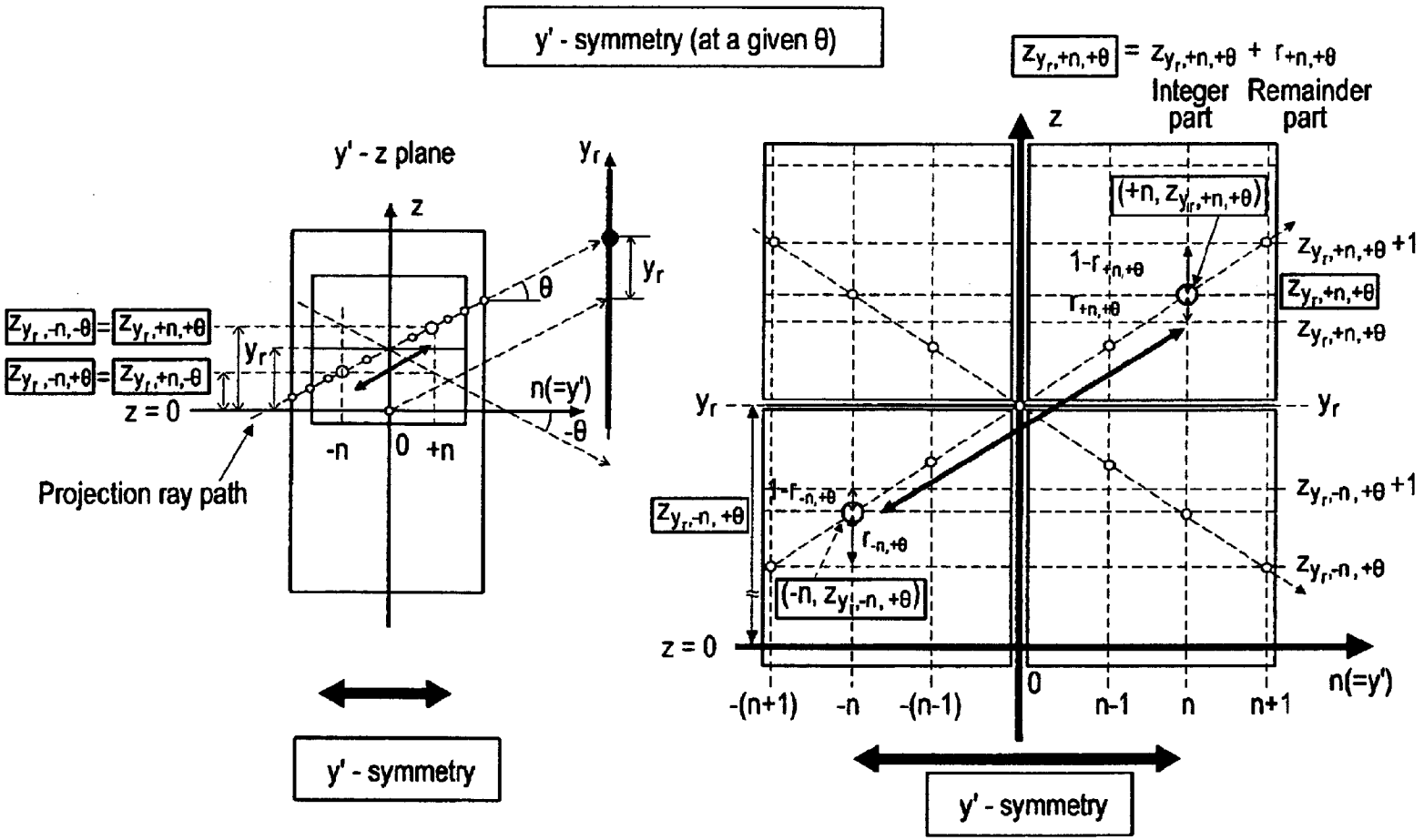
FIG. 5A illustrates the y'-symmetry in the proposed SSP method.

(c) y'-symmetry (+n and −n, see FIG. 5A)

Unlike mirror- and $\phi$-symmetry, y'- and $\theta$-symmetry are in the y'-z plane. It should be noted that y'-symmetry is intimately related to $\theta$-symmetry. Therefore, it is easy to illustrate the two together, as follows. The y'-symmetry property has the effect of changing the interpolation coefficients to complementary values. In fact, y'-symmetry has the same symmetry property as $\theta$-symmetry, as discussed below. First, the property of y'-symmetry is illustrated in FIG. 5A. As shown in FIG. 5A, variable Z can now be noted as follows (see also FIG. 3):

$$z_{y_r,n,\theta}=y_r+n\tan\theta=Z_{y_r,n,\theta}+r_{y_r,n,\theta} \tag{11}$$

where $n, Z_{y_r,n,\theta}$ *and* $y_r \in$ INTEGER $r_{y_r,n,\theta} \in$ REAL and $0 \leqq r_{y_r,n,\theta} < 1$ $$\begin{aligned} z_{y_r,n,\theta}+z_{y_r,-n,\theta} &= (y_r+n\tan\theta)+(y_r-n\tan\theta) \\ &= Z_{y_r,n,\theta}+r_{y_r,n,\theta}+Z_{y_r,-n,\theta}+r_{y_r,-n,\theta} \\ &= 2y_r \in \text{INTEGER} \end{aligned} \tag{12}$$

$$\therefore r_{y_r,n,\theta}+r_{y_r,-n,\theta}=1$$

$$r_{y_r,-n,\theta}=1-r_{y_r,n,\theta}$$

where $r_{y_r,n,\theta}$ and $1-r_{y_r,n,\theta}$ represent die interpolation coefficients.

Using this symmetry, two interpolation operations can be simultaneously performed, thereby reducing the number of loops in y'(=n) by half. Therefore, (5) can be rewritten as follows:

$$P_{\phi,\theta}(x_r, y_r) = I(x_r, 0, y_r) + \sum_{n=1}^{N_{I_{x_r}}/2} \begin{bmatrix} I(x_r, n, Z_{y_r,n,\theta})(1-r_{y_r,n,\theta}) + \\ I(x_r, n, Z_{y_r,n,\theta}+1)r_{y_r,n,\theta} + \\ I(x_r, -n, Z_{y_r,-n,\theta})(1-r_{y_r,-n,\theta}) + \\ I(x_r, -n, Z_{y_r,-n,\theta}+1)r_{y_r,-n,\theta} \end{bmatrix} \tag{13}$$

Equation (13) can be transformed into a factored form to reduce the number of instructions required to execute the computation. Furthermore, the interpolation coefficient $r_{y_r,n,\theta}$ can be reduced to simple functions of only n and $\theta$ and can be derived from (11). Because $y_r$ is always an integer and $r_{y_r,n,\theta}$ satisfies the condition $0 \leqq r_{y_r,n,\theta} < 1$, $r_{y_r,n,\theta}$ is a function of only n and $\theta$. Therefore, the notation $r_{y_r,n,\theta}$ can be simplified to $r_{n,\theta}$ (see and compare with FIGS. 3 and 5A). Further, $(1-r_{y_r,n,\theta})$ is equal to $r_{y_r,-n,\theta}$. Similarly, $(1-r_{y_r,-n,\theta})$ is equal to $r_{n,\theta}$. Using the simplified forms, (13) can be transformed to a factored form, as shown below:

$$P_{\phi,\theta}(x_r, y_r) = \tag{14}$$

$$I(x_r, 0, y_r) + \sum_{x=1}^{N_{I_{x_r}}/2} \begin{bmatrix} \{I(x_r, n, Z_{y_r,n,\theta}) + \\ I(x_r, -n, Z_{y_r,-n,\theta}+1)\}(1-r_{n,\theta}) + \\ \{I(x_r, n, Z_{y_r,n,\theta}+1) + I(x_r, -n, Z_{y_r,-n,\theta})\}r_{n,\theta} \end{bmatrix}$$

Figure 5B:
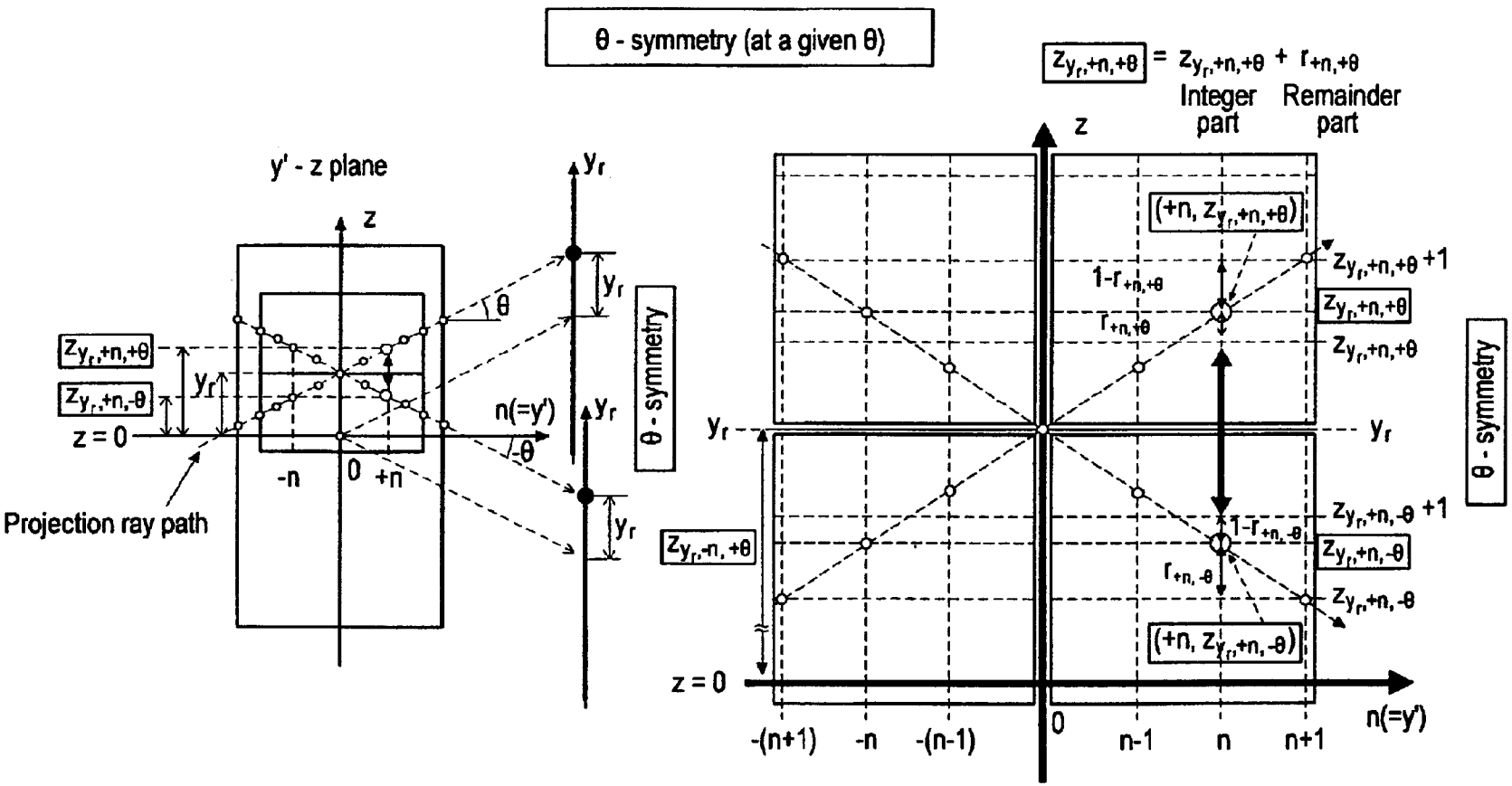
FIG. 5B illustrates the θ-symmetry in the proposed SSP method.

(d) $\theta$-symmetry ($+\theta$ and $-\theta$, see FIG. 5B)

Now, let us illustrate how the $\theta$-symmetry shares the calculation of interpolation coefficients with the y'-symmetry discussed above. As shown in FIG. 5B, only the changes in the interpolation coefficients change their own complementary values when the signs of $\theta$ change.

Using (4), (5), (11) and (12), it can be shown that z and r are given as:

$$\begin{aligned} z_{y_r,n,\theta} &= y_r + n\tan\theta \\ &= y_r + (-n)\tan(-\theta) \\ &= z_{y_r,-n,-\theta} \\ z_{y_r,n,-\theta} &= y_r + n\tan(-\theta) \\ &= y_r + (-n)\tan\theta \\ &= z_{y_r,-n,\theta} \end{aligned} \tag{15}$$

Therefore, $$r_{-n,\theta} = r_{n,-\theta} = 1 - r_{n,\theta}$$

$$r_{-n,-\theta} = r_{n,\theta}$$

$$Z_{y_r,n,\theta} = Z_{y_r,-n,-\theta}$$

$$Z_{y_r,n,-\theta} = Z_{y_r,-n,\theta}$$

Using the relation given in (15), (14) can be written as follows:

$$P_{\phi,-\theta}(x_r, y_r) = \tag{16}$$

$$I(x_r, 0, y_r) + \sum_{n=1}^{N_{I_{x_r}}/2} \begin{bmatrix} \left\{ \begin{matrix} I(x_r, n, Z_{y_r,n,-\theta}) + \\ I(x_r, -n, Z_{y_r,-n,-\theta}+1) \end{matrix} \right\}(1-r_{n,-\theta}) + \\ \left\{ \begin{matrix} I(x_r, n, Z_{y_r,n,-\theta}+1) + \\ I(x_r, -n, Z_{y_r,-n,-\theta}) \end{matrix} \right\}r_{n,-\theta} \end{bmatrix}$$

$$=$$

$$I(x_r, 0, y_r) + \sum_{n=1}^{N_{I_{x_r}}/2} \begin{bmatrix} \left\{ \begin{matrix} I(x_r, n, Z_{y_r,-n,\theta}) + \\ I(x_r, -n, Z_{y_r,n,\theta}+1) \end{matrix} \right\}r_{n,\theta} + \\ \left\{ \begin{matrix} I(x_r, n, Z_{y_r,-n,\theta}+1) + \\ I(x_r, -n, Z_{y_r,n,\theta}) \end{matrix} \right\}(1-r_{n,\theta}) \end{bmatrix}$$

Equation (14) is for $P_{\phi,\theta}(x_r,y_r)$, while (16) is for the $P_{\phi,-\theta}(x_r,y_r)$. For the computation of (16), the relations given in (15), i.e., $r_{n,\theta}$, $r_{n,-\theta}$, $Z_{y_r,n,\theta}$, and $Z_{y_r,n,-\theta}$ can be used once again and further simultaneously calculate $P_{\phi,\theta}(x_r,y_r)$ and $P_{\phi,-\theta(xr}, y_r)$.

As shown above, y'- and θ-symmetries share the common properties. The y'-symmetry, therefore, is used to reduce the number of loop counts y'(=n), while the θ-symmetry is used to reduce the number of loop counts θ.

In summary, a total of sixteen points of symmetry for the SSP method, namely, 2 (Mirror-symmetry), 2 (ϕ+90° symmetry), 2 (y'-symmetry) and 2 (θ-symmetry), are used. Thus, multiplication of these leads to 16. In addition to these symmetry based reductions in computation time (16 times), as will be detailed, SIMD will speed-up the computation further by another factor of 4. As such, a total speed gain of 64 (16×4) has been achieved with the new SSP method.

FIG. 5 illustrates y'- and/or θ-symmetry in the proposed SSP method. FIG. 5A shows y'-symmetry, while FIG. 5B shows θ-symmetry. The left side of each figure shows the z-y' plane cut-view, while the right part shows an expanded view of the left. Each quarter illustrates the details of the interpolation coefficient, r's. This y'- or θ-symmetry property indicates that if one of the interpolation coefficients is calculated for one point, then the remaining interpolation coefficients for the other three points can be obtained without additional computation. The amount of calculations, therefore, can be reduced to one fourth (¼) by using y'- and θ-symmetries.

Parallelization of Computation using SIMD for SSP method

A. SIMD (Single Instruction Multiple Data) and Symmetry Properties

It is important to reduce the number of instructions per loop for practical purposes, while reducing the number of loops within the projector/backprojector, to realize a fast algorithm. The number of instructions per loop was reduced by using the SIMD technique. The use of SIMD reduces the number of instructions per loop, thereby reducing the overall computation time by a factor of four. The operand of SIMD should be determined carefully to improve the efficiency. As shown above, projection/backprojection of sixteen points were simultaneously performed. For this operation, sixteen symmetry points were divided by two groups, one for +θ and the other for −θ. Since a single SIMD instruction data set consists of four data sets, each group having the same (+θ or −θ), was coupled to one of the two SIMD instruction datasets.

Figure 12:
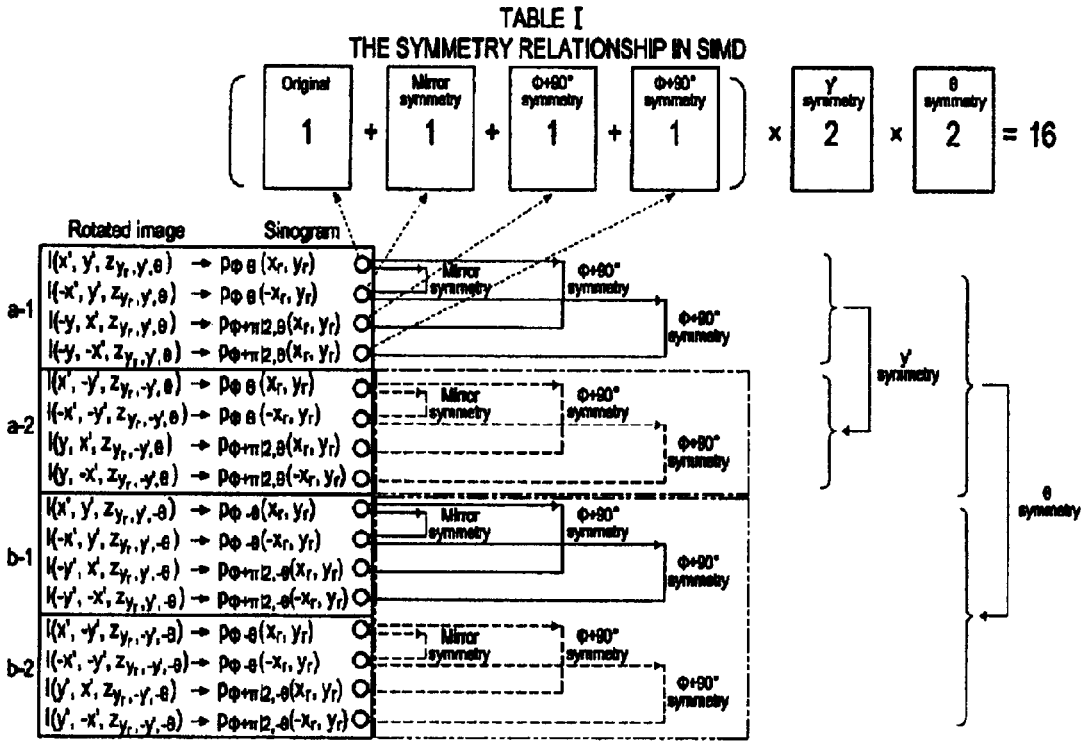
FIG. 12 illustrates the symmetry relationship in SIMD.

These two groups having the same θ is based on (14) and (16). FIG. 12 shows these sixteen pairs of symmetry relationship between rotated image data sets and projection data sets. The upper group (a-1 and a-2) shares the same θ, while the lower group shares −θ. Each group is divided by two sub-groups. Each upper subgroup shares the same linear-interpolation coefficients, while each lower group shares the complementary values to that of the each upper group. Each single subgroup, therefore, can be handled as a single SIMD data set (or single SLMD pack). $Z_{y_r,y',\theta}$ and $z_{y_r,-y',-\theta}$ share the same value. Similarly, $z_{y_r,y',\theta}$ and $z_{y_r,-y',\theta}$ also share the same value.

As noted above, sixteen symmetry pairs are divided into two groups, each sharing the same θ. In addition, these two groups were once again divided into two subgroups. The members of subgroups a-1 and b-2 share the same interpolation coefficient (e.g., $r_{y',\theta}$), while the subgroup a-2 and b-1 have complementary values (e.g., $1-r_{y',\theta}$) as interpolation coefficients. Each subgroup represents one packed SIMD data, as shown below:

$$SI_{x'}(n, z) = \{I(x', n, z), I(-x', n, z), I(-n', x', z), I(-n, -x', z)\} \tag{17}$$

$$SI_{x'}(-n, z) = \{I(x', -n, z), I(-x', -n, z), I(n, x', z), I(n, -x', z)\}$$

$$(SP)_{\phi,\theta}(x_r, y_r) = \left\{P_{\phi,\theta}(x_r, y_r), P_{\phi,\theta}(-x_r, y_r), P_{\phi+\frac{\pi}{2},\theta}(x_r, y_r), P_{\phi+\frac{\pi}{2},\theta}(-x_r, y_r),\right\}$$

$$(SP)_{\phi,-\theta}(x_r, y_r) = \left\{P_{\phi,-\theta}(x_r, y_r), P_{\phi,-\theta}(-x_r, y_r), P_{\phi+\frac{\pi}{2},\theta}(x_r, y_r), P_{\phi+\frac{\pi}{2},\theta}(-x_r, y_r),\right\}$$

where

SI means an SIMD image data set.

SP means an SIMD projection data set.

Equation (17) shows the arrangement of the SIMD data set for the upper group of FIG. 12. This process is referred to as packing and single SIMD instruction data set consists of four points. This process can be applied to the lower groups having −θ.

As noted above, the upper group and the lower group of FIG. 12 are based on (14) and (16). Equations (14) and (16) can now be transformed into SIMD versions as given in (17), as shown below:

$$(SP)_{\phi,\theta}(x_r, y_r) = (SI)_{x_r}(0, y_r) + \sum_{n=1}^{N_{I_{x_r}}/2} \left[ \begin{array}{c} (1 - r_{n,\theta})\{(SI)_{x_r}(n, Z_{y_r,n,\theta}) + (SI)_{x_r}(-n, Z_{y_r,-n,\theta} + 1)\} + \\ r_{n,\theta}\{(SI)_{x_r}(n, Z_{y_r,n,\theta} + 1) + (SI)_{x_r}(-n, Z_{y_r,-n,\theta})\} \end{array} \right] \tag{18}$$

$$(SP)_{\phi,-\theta}(x_r, y_r) = (SI)_{x_r}(0, y_r) + \sum_{n=1}^{N_{I_{x_r}}/2} \left[ \begin{array}{c} (1 - r_{n,\theta})\{(SI)_{x_r}(n, Z_{y_r,-n,\theta} + 1) + (SI)_{x_r}(-n, Z_{y_r,n,\theta})\} + \\ r_{n,\theta}\{(SI)_{x_r}(n, Z_{y_r,-n,\theta}) + (SI)_{x_r}(-n, Z_{y_r,n,\theta} + 1)\} \end{array} \right]$$

where $SI_{x_r}(n,Z_{y_r,n,\theta})$, $SI_{x_r}(n,Z_{y_r,n,\theta}+1)$ and $SP_{\phi,\theta(xr},y_r)$ are according to subgroup "a-1" of FIG. 12.

$SI_{x_r}(-n,Z_{y_r,-n,\theta})$, $SI_{x_r}(-n,Z_{y_r},-n\theta+1)$ and $SP_{\phi,\theta}(x_r,y_r)$ are according to subgroup "a-2" of FIG. 12.

$SI_{x_r}(n,Z_{y_r,-n,\theta})$, $SI_{x_r}(n,Z_{Y_r,-n,\theta}+1)$ and $SP_{\phi,-\theta}(x_r,y_r)$ are according to subgroup "b-1" of FIG. 12.

$SI_{x_r}(-n,Z_{r_r,n,\theta})$, $SI_{x_r}(-n,Z_{y_r,n,\theta}+1)$ and $SP_{\phi,-\theta}(x_r,y_r)$ are according to subgroup "b-2" of FIG. 12.

$Z_{y_r,n,\theta}=Z_{y_r,-n,-\theta}$ $Z_{y_r,m,n,\theta}=Z_{y_r,n,-\theta}$

This SIMD packing concept can be applied equally to a backward projection.

As a precaution, it should be noted that there are several special cases within the above symmetric pairs. These special cases indicate that some symmetry pairs will share the same rotating image point, thereby resulting in errors. TABLE II shows these special cases, which require special attention and correction.

TABLE II

THE SPECIAL CASES WITHOUT SYMMETRY COUNTERPART

| | Symmetry pairs on image plane | Special case |
|---|---|---|
| ϕ-symmetry | $I(x',y',z_{y_r,y',\theta})$ and $I(-y',x',z_{y_r,y',\theta})$ | The points of x' = y' |
| Mirror symmetry | $I(x',y',z_{y_r,y',\theta})$ and $I(-x',y',z_{y_r,y',\theta})$ | The points of x' = 0 |
| ϕ-symmetry | $I(x',y',z_{y_r,y',\theta})$ and $I(x',=y',z_{y_r,y',\theta})$ | The points of y' = 0 |

B. Optimization of Job Distribution in Multi-Processor Environment

The recently available PC provides a multi-processor environment. To utilize this parallel computation capability, an instruction called "thread programming technique" can be used. The proposed SSP method is capable of being expanded to multi-processor systems. In this case, a job distribution with an equal amount of load is important for optimal performance.

As the method according to the present invention is based on the assumption of circular cylindrical FOV, the job load is designed to be distributed equally along the x' or $x_r$ axis. This is because there is uneven distribution of computational load if an equal range of x' is assigned to each CPU, as illustrated in FIG. 6.

Figure 6:
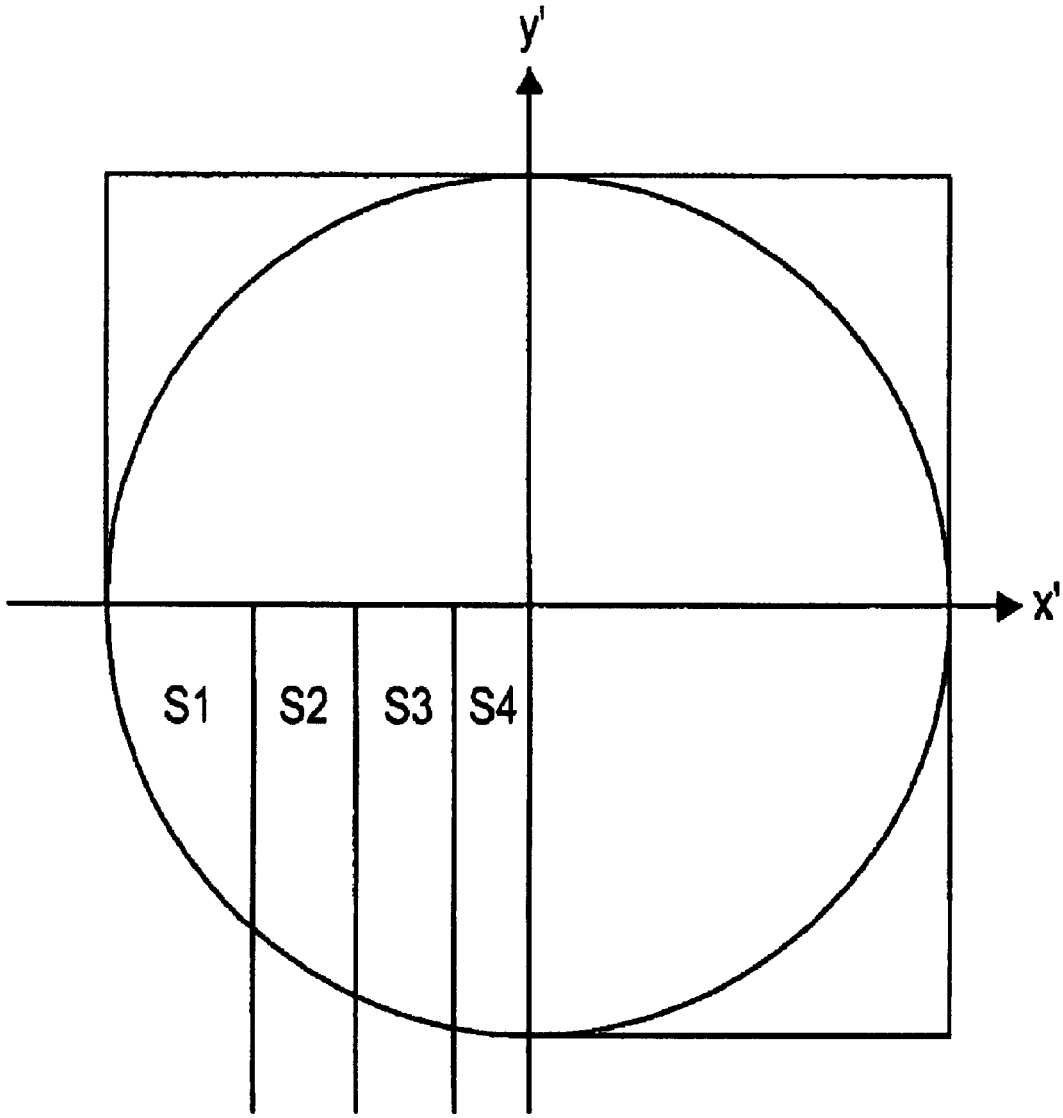
FIG. 6 illustrates the concept of the balanced job distribution based on the sum of the ray path length.

FIG. 6 illustrates the concept of the balanced job distribution based on the sums of the ray path length, that is, equal distribution of the computational load for each group S1, S2, S3 and S4. In this case, the job loads are divided into four groups of equal area, i.e., S1, S2, S3 and S4. This redistribution suggests that each group has almost the same area, i.e., the same amount of computational load.

Description of the Overall Method

Figure 7:
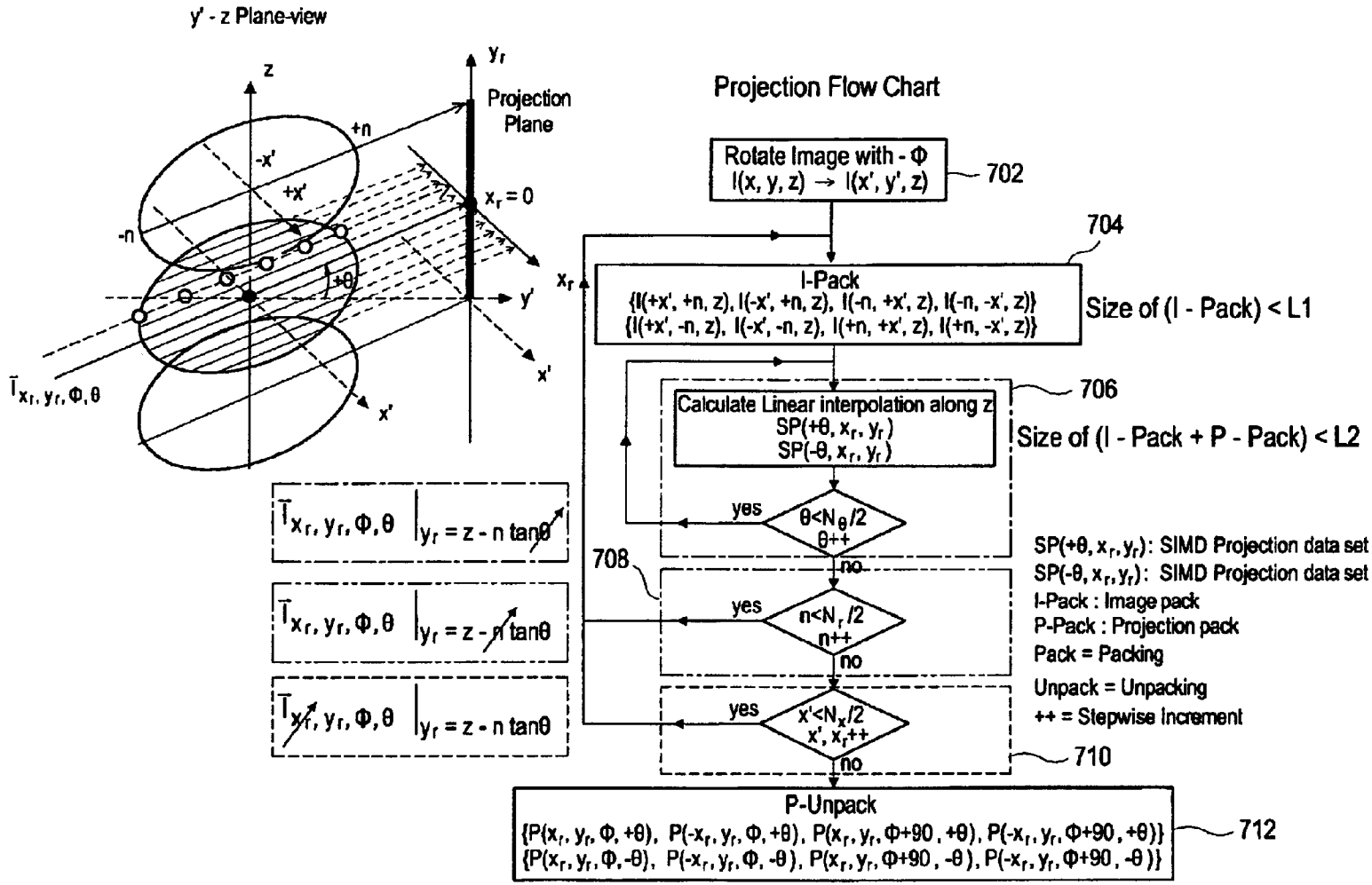
FIG. 7 is a flow chart of the projection according to an embodiment of the present invention.
Figure 8:
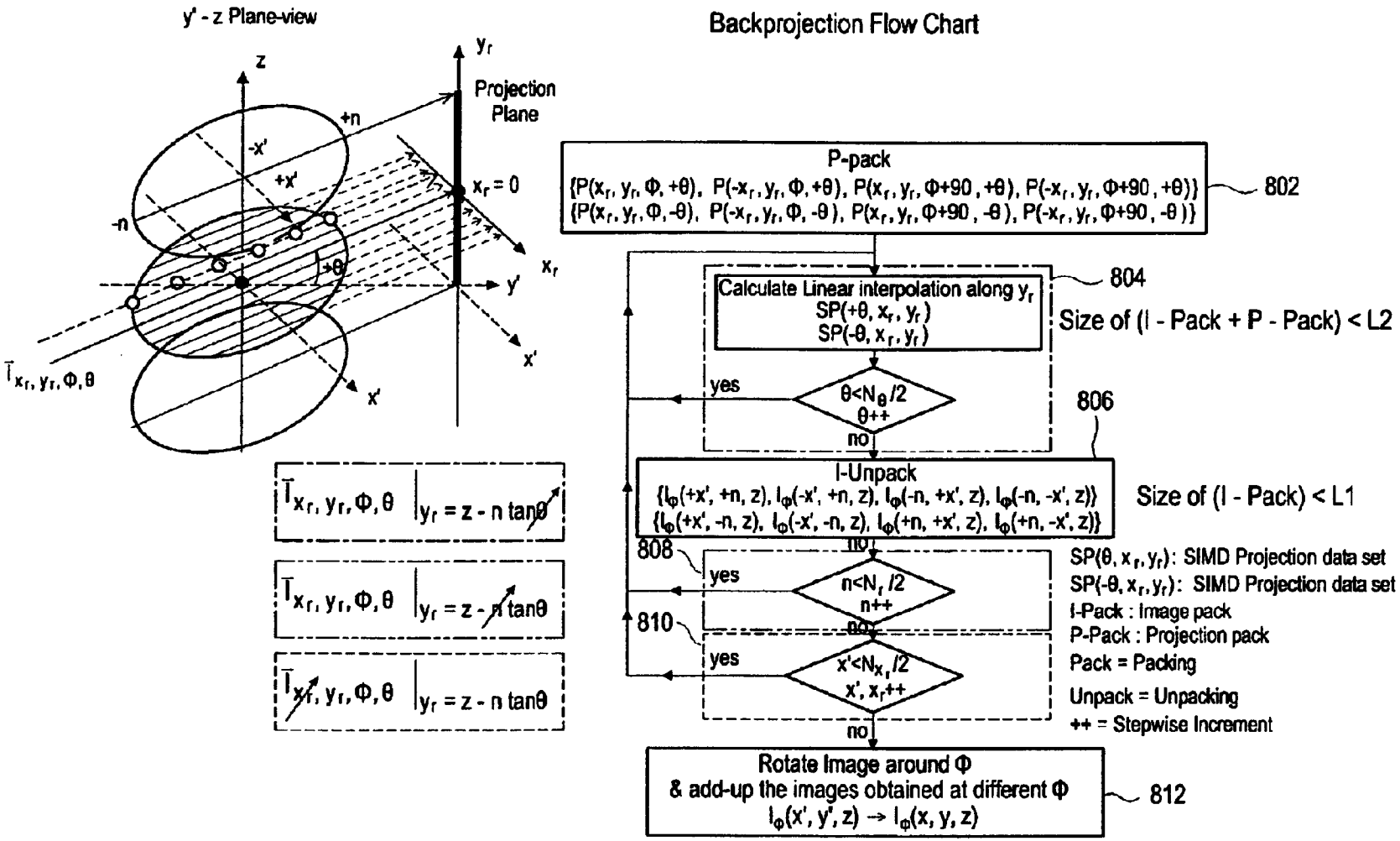
FIG. 8 is a flow chart of the back-projection according to an embodiment of the present invention.

The schematics of the new SSP projector and backprojector are provided in FIGS. 7 and 8, respectively. For SSP, the aligned frame was used by utilizing the rotation operation as well as the symmetry properties to reduce the number of loop counts. In addition, the total number of instructions was reduced by combining the symmetry properties and SIMD technique.

FIG. 7 is a flow chart showing the projection. The innermost block 706 within the loop includes z loop, the interpolation operation, the integration along the ray path 708 and scanning along the x' axis 710. After the projection for the entire θ range, the intermediate results of rotated projection should be unpacked in order to be stored back to the original position. It should be noted that the sizes of (I-Pack) and SIMD data sets (I-Pack+P-Pack) must be less than the cache sizes of L1 and L2, respectively, in order to maximize the cache hit ratio and the data access speed.

FIG. 8 is a flow chart showing the backprojection. First, 8 projection data, which have symmetric relationships, are packed for use in the SIMD. These packed projection data, P-Pack, are interpolated linearly along the $y_r$ direction to calculate the packed backprojected image data, I-Pack, for the semifinal image $I_\phi$ (x',y',z) for all θ directions. As an intermediate step, these packed backprojected image data are unpacked and aligned to each valid position in the semifinal image data $I_\phi$ (x',y',z) after each step of θ loop. These procedures are repeated by loops of $y_r$ and $x_r$ until the semifinal image $I_\phi$ (x',y',z) is fully reconstructed. The semifinal image $I_\phi$ (x',y',z) is reconstructed for each view angle, ϕ. Each semi-final image $I_\phi$ (x',y',z) is rotated by its own view angle θ and then added up to reconstruct the final image I (x,y,z), the image at the original Cartesian coordinates. Similar to the projection operation, the sizes of SIMD data sets, (I-Pack+P-Pack) and (I-Pack) should be less than the cache sizes of L2 and L1, respectively, for the maximization of the computation.

As shown in FIG. 7 and FIG. 8, the rotation operation was used to utilize the aligned frame. Before the projection step, the projection plane is aligned with the aligned from (x',y') and each incoming image plane is then rotated according to its respective view angle. After the backprojection step, the original image is recovered from the aligned frame by rotating back to the original view angle, thus permitting an intermediate reconstructed image data to be formed.

To reduce processing time, the efficient use of cache was found to be an important factor in the overall computation. Memory allocation and loop orders should be optimized for the memory access pattern. Since $x_r$(=x') is set to the variable of the outermost loop, the memory stride on read and write can be confined to a certain range within the L2 cache size. Furthermore, the variable of the innermost loop should be z or $y_r$, since most of the computation intensive operations in the SSP method are related to interpolation of z or $y_r$. Therefore, it is desirable to allocate the initial memory by the order [x']:[y']:[z] for backprojection while for projection, the order should be [ϕ]:[$x_r$]:[θ]:[$y_r$]. These memory allocations, therefore, will determine the loop orders. These loop orders of projector/backprojector are also depicted in FIG. 7 and FIG. 8. As a result of using these symmetries, the total number of loop counts can be reduced by half at each step.

For the SIMD, a memory packing (step) is performed prior to each projection/backprojection step. After the projection step, the packed SIMD data set in the projection domain is unpacked and returned to the original position. Similarly, the packed SIMD data set in the image domain is unpacked after each backprojection step.

Experimental Results

A. Methods

To evaluate the efficiency of the SSP method, the data or sonogram was applied to HRRT (High Resolution Research Tomograph developed by CPS/Siemens, Knoxville, Tenn., U.S.A). HRRT has 119,808 detectors and is designed for ultra high resolution brain scanning. Since HRRT has the largest number of detectors (with the smallest detectors size) among the human PET scanners that are currently available, it has the highest computational complexity for image reconstruction. The number of computations has been increased substantially (in proportion to the number of LORs) and is much larger compared to other existing PET scanners. The reconstruction software provided by the HRRT package supports iterative algorithms such as OP-OSEM3D and is the preferred reconstruction algorithm in the HRRT system. One of the advantages of OP-OSEM3D, among others, is preventing the occurrence of negative bias when the random rate is high. This algorithm was chosen to test the performance of our new SSP method since it requires the largest memory size and is the most computation-intensive algorithm. Therefore, unless otherwise specified, the HRRT OP-OSEM3D package S/W will be referred to as the existing method.

As can be seen, the SSP method is supported by commercially available computer systems such as a common PC. Three other platforms were chosen to compare the SSP method against the existing method. The first platform is PC 1, which has Intel dual-core 3.0 GHz, 4 GB RAM, 1 MB L2 cache per CPU. The second platform, PC2, is a high-end PC with two dual-core AMD 2.4 GHz, 8 GB RAM, 1 MB L2 cache per CPU. The third platform is the current HRRT computer platform, which consists of an eight node cluster system (this is denoted as HRRT CPS system), wherein each node consists of two Xeon 3.06 GHz processors with 512 KB L2 cache and 2 GB RAM.

The concept of "span" in 3D means the mode of axial compression. The test was performed in span 3 and span 9, which are typically used in HRRT. The parameters for OP-OSEM3D are as follows: 256×256×207 image pixels; six iterations; and 16 subsets. Thread programming is also used.

B. Results

Before discussing the computational speed, the accuracy of the reconstructed images (compared to the original HRRT package provided by CPS/Siemens) appears to have been emphasized. First, the results of the projector and backprojector of the SSP were compared with the existing HRRT package. As shown in FIGS. 9 and 10, only a little difference was found. As mentioned previously, the SSP technique or method is basically a tri-linear interpolation, whereas the existing method is a bi-linear method. FIG. 9B shows the profiles for projection data at 45° and 90°. The same comparison was made on the backprojection data as well as the final reconstructed images, wherein the results are shown in FIGS. 10 and 11. As shown therein, the projected data and image quality of SSP are equivalent to the existing method, but yet with an advantage of nearly two orders of magnitude in computational speed.

The performance aspect of the SSP method (i.e., execution time on PC 1 and 2) was also compared. The computation time was measured for the two existing compression modes, namely, span 3 and span 9. The results indicate that the SSP method, as expected, indeed enhanced the performance by almost 80 times, 2 ($\phi$+90° symmetry)×2 ($x_r$ or mirror-symmetry)×2 (y'-symmetry)×2 ($\theta$-symmetry)×4 (SIMD)+other optimizations, compared to the existing method (original HRRT package). It should be noted that this performance enhancement can be obtained more or less independent of the system architecture. Furthermore, as the method suggests, the relative improvement will be higher as more oblique rays or angles are used, as seen from TABLES III and IV.

Figure 9A:
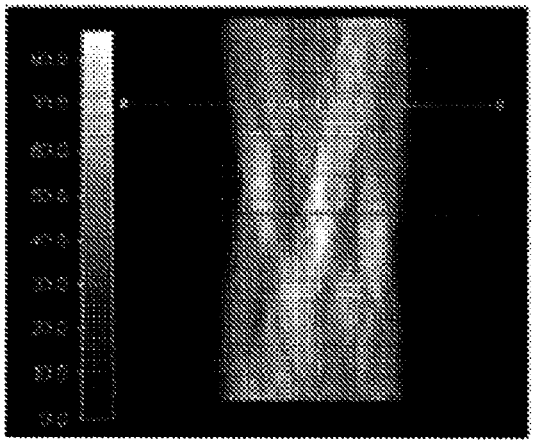
FIG. 9A illustrates a comparison of projection data between the existing method and the proposed SSP method.
Figure 9A:
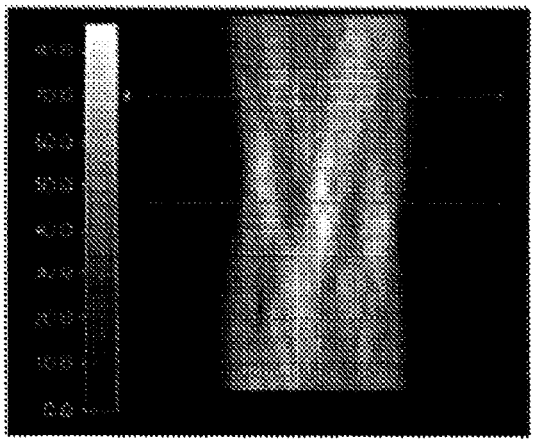
Figure 9A:
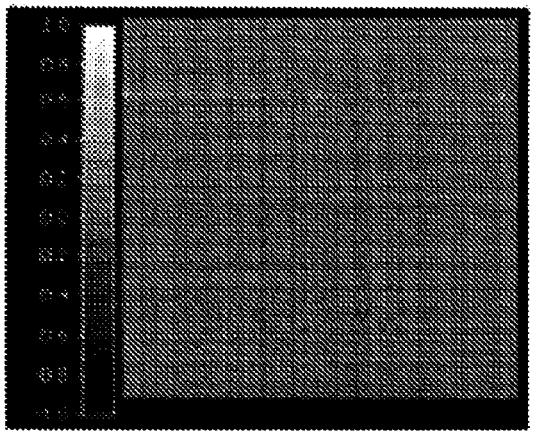
Figure 9B:
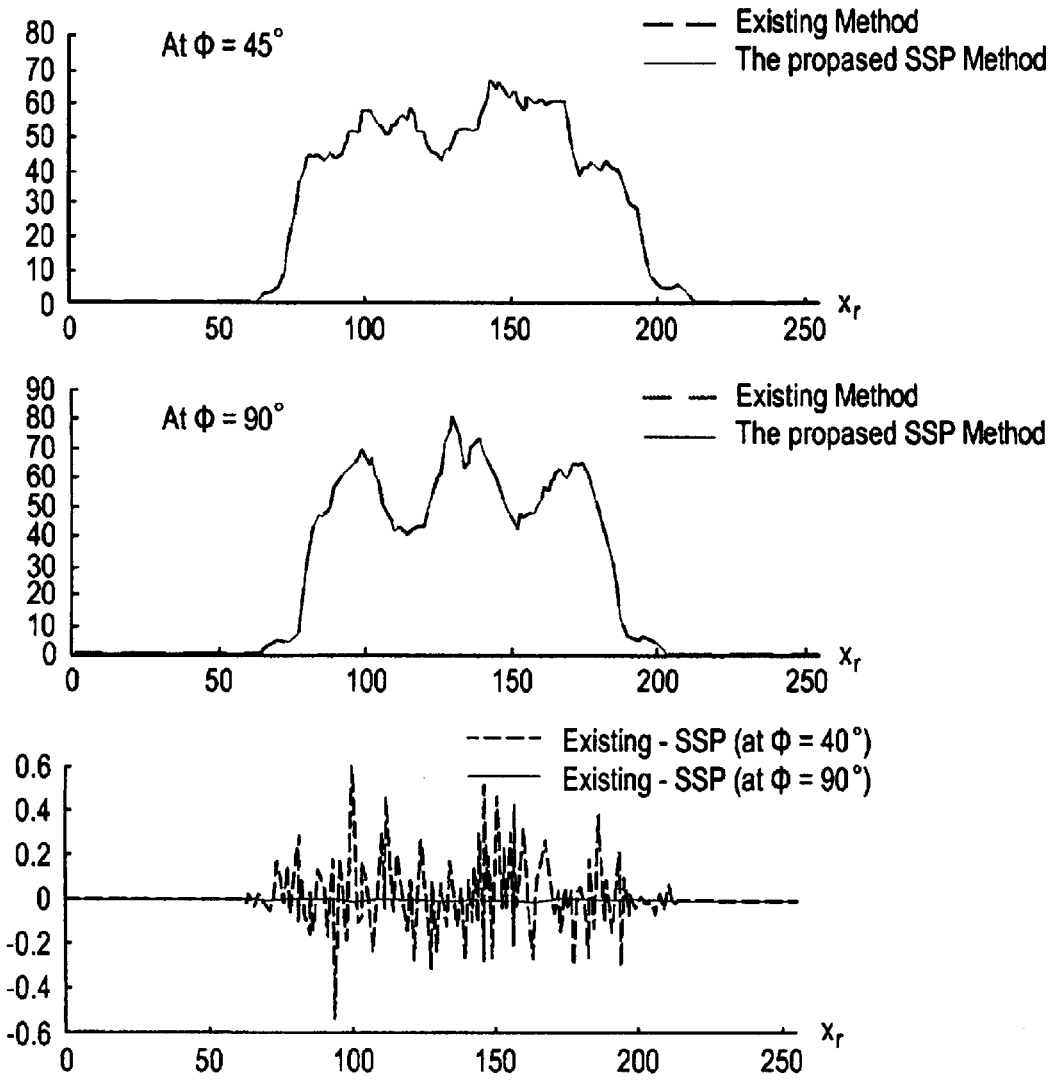
FIG. 9B illustrates cut-views of sinogram at a specific view.

FIG. 9A illustrates a comparison of projection data between the existing method and the proposed SSP method. (Top: Existing, Middle: SSP, Bottom: The difference between SSP and the existing method) FIG. 9B illustrates the cut-views of sinogram at a specific view. (Cop: Comparison at $\phi$=45°, Middle: Comparison at $\phi$=90°, Bottom: The differences between SSP and the existing method at $\phi$=45° and $\phi$=90°, respectively).

Figure 10A:
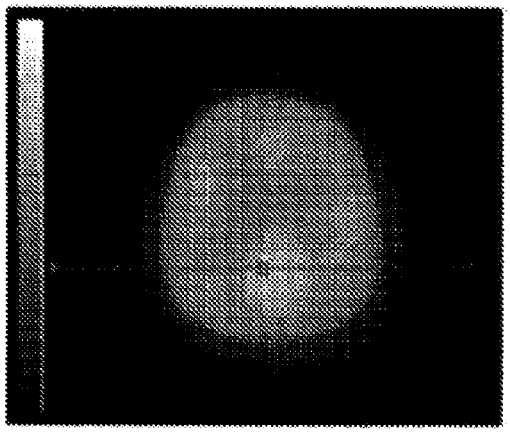
FIG. 10A illustrates a comparison of simple back-projection images between the existing method and the proposed SSP method.
Figure 10A:
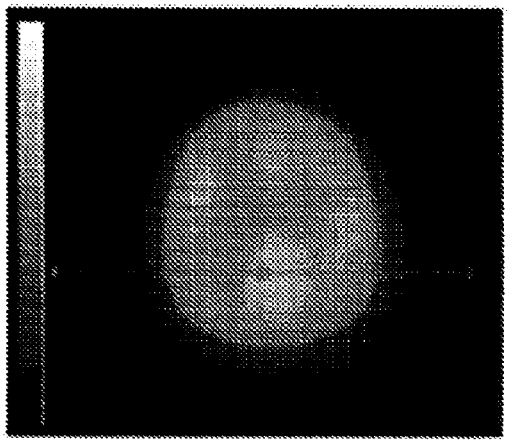
Figure 10A:
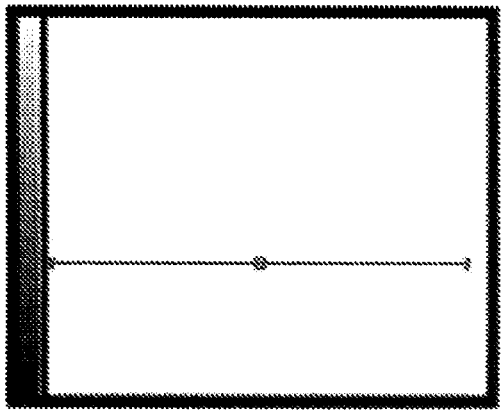
Figure 10B:
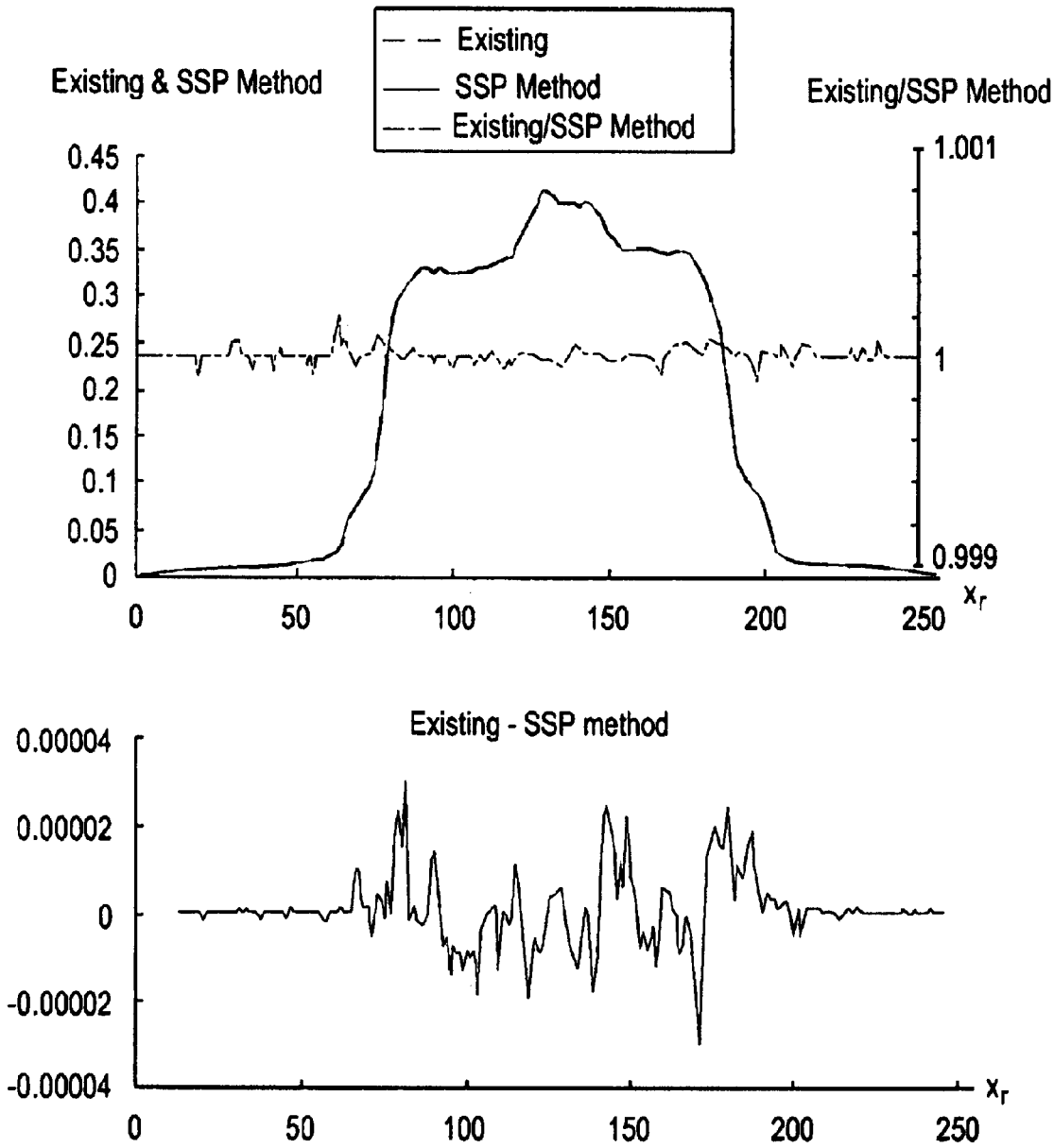
FIG. 10B illustrates cut-views (profiles) at an x axis (y=154, z=103).

FIG. 10A illustrates a comparison of simple backprojection images between the existing method and the proposed SSP method. (Top: Existing method. Middle: New SSP technique. Bottom: The differences) FIG. 10B illustrates the cut-views (profiles) at an x axis (y=154, z=103). (Top: Comparison between the existing and new SSP. Bottom: The differences between the two)

Figure 11A:
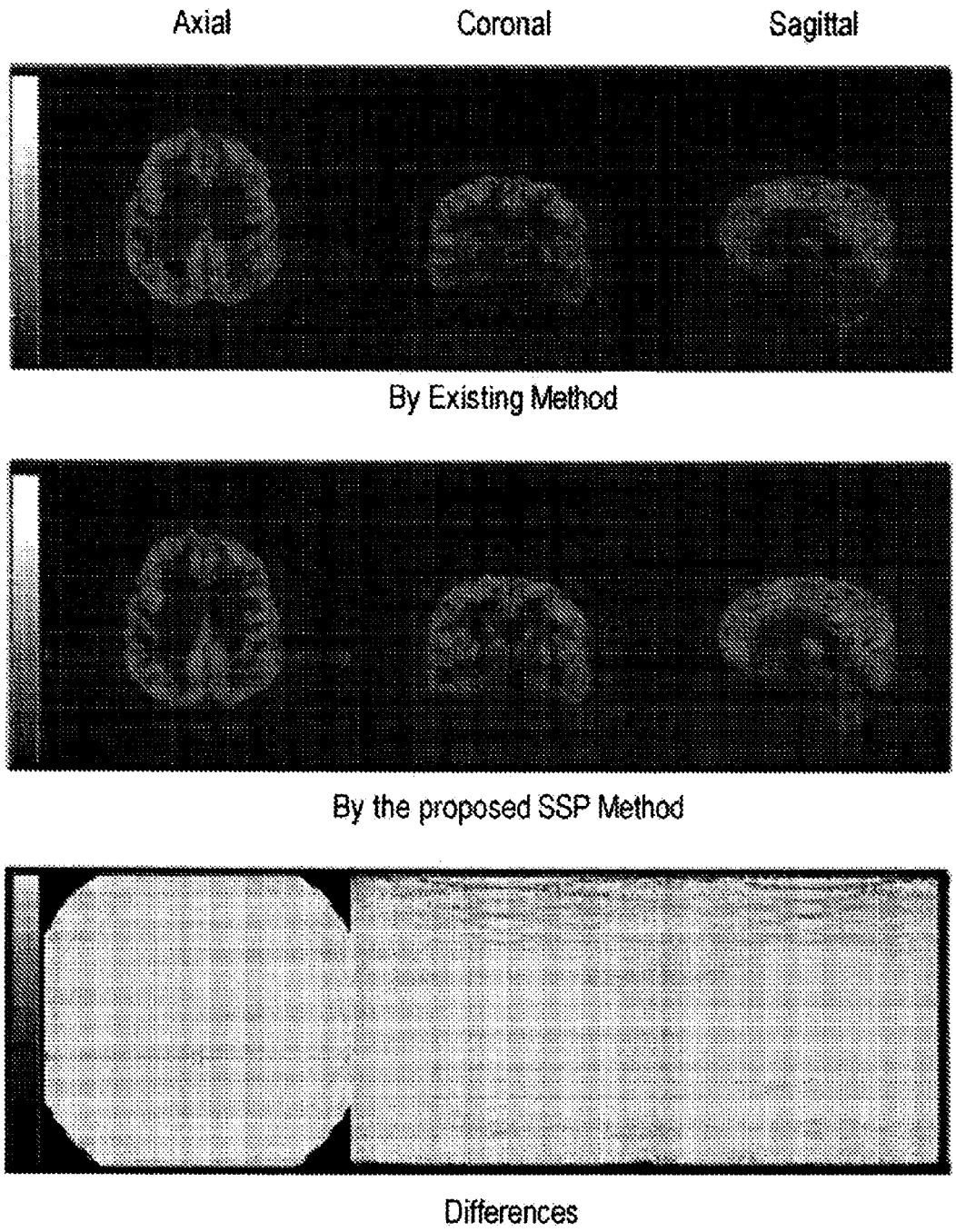
FIG. 11A illustrates a set of reconstructed images with the existing method, the proposed SSP method and the differences.
Figure 11B:
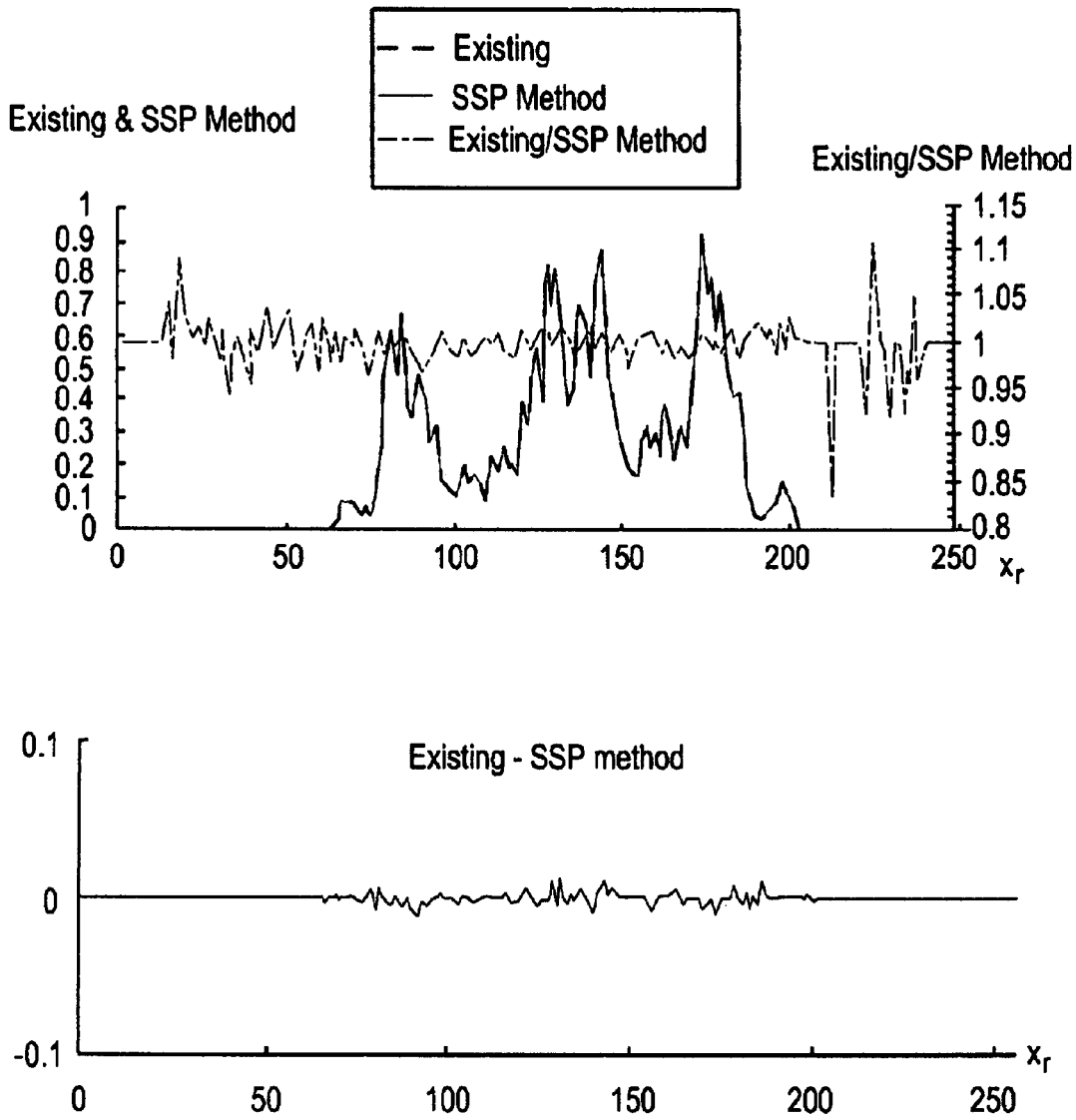
FIG. 11B illustrates cut-views (profiles) at an x axis (y=154, z=103).

FIG. 11 illustrates a comparison of reconstructed images with six iterations and their differences. FIG. 11A illustrates a set of reconstructed images with the existing method (top), with new SSP method (middle) and the differences (bottom). FIG. 11B illustrates the cut-views (profiles) at an x axis (y=154, z=103).

TABLE III

THE COMPARISONS OF RUNNING TIME OF THE VARIOUS OPERATIONS ON PC1.

| | Existing | new | ratio |
|---|---|---|---|
| Projection (span 9) | 1539(s) | 24(s) | 64.1 |
| Backprojection (span 9) | 1527(s) | 25(s) | 61.1 |
| Projection (span 3) | 4276(s) | 51(s) | 83.8 |
| Backprojection (span 3) | 4255(s) | 53(s) | 80.3 |
| Projection + backprojection (span 9) | 3066(s) | 49(s) | 62.6 |
| Projection + backprojection (span 3) | 8531(s) | 104(s) | 82.0 |

PC1: Intel 3.0 GHz 1 dual-core CPU, 4 GB RAM, 1 MB L2 cache per CPU.

TABLE IV

THE COMPARISONS OF RUNNING TIME OF THE VARIOUS OPERATIONS ON PC2

| | Existing | new | ratio |
|---|---|---|---|
| Projection (span 9) | 556(s) | 9(s) | 61.8 |
| Backprojection (span 9) | 679(s) | 11(s) | 61.7 |
| Projection (span 3) | 1600(s) | 22(s) | 72.2 |
| Backprojection (span 3) | 1767(s) | 22(s) | 80.3 |
| Projection + backprojection (span 9) | 1235(s) | 20(s) | 61.7 |
| Projection + backprojection (span 3) | 3608(s) | 44(s) | 82 |

PC2: AMD 2.4 Ghz 2 dual-core CPU, 8 GB RAM, 1 MB L2 cache per CPU.

The use of more oblique rays or angles (e.g., span 3) results in better axial resolution and statistics. Since reconstruction using the EM algorithm consists of a large number of projections and backprojections, this improvement in speed is especially important. Finally, a comparative study of the HRRT CPS system was compared with the original HRRT CPS algorithm vs. our 2 dual core CPU (without cluster) configuration, PC2, with the SSP method and obtained a speed gain of a factor of 9 to 11. The reason for the differences between the calculation (64 times) and the actual system based computation (9-11 times) is probably due to the 16 Xeon-CPUs based original HRRT CPS system. The HRRT CPS system having 16 Xeon-CPUs is much more powerful than PC2 having only 2 dual-core CPUs. This H/W difference could have been the result of such reduced speed gain. In addition, SSP method can easily extend to the cluster version.

The proposed SSP method will improve the overall computation time, especially when a dynamic functional study is desired. Currently, the image reconstruction time for a normal HRRT PET scan with a commercially available PC (PC2 type) requires about seven to eight minutes for span 3 after completing the sinogram formation and the precorrection processes compared with eighty minutes with current HRRT reconstruction package (OP-OSEM3D) utilizing an 8-node cluster system.

CONCLUSION

The present invention provides a fast method of calculating the ray path, which leads to the projection data and reconstructed image in 3D by using the symmetry properties of the projection and image data. Exploiting these simple geometrical symmetry properties and with the help of SIMD, a new ultra fast reconstruction method was developed, which has a computational speed advantage of nearly two orders of magnitudes compared to the existing reconstruction package (specifically that of OP-OSEM3D, the latest and most widely used PET method, especially for HRRT without compromising image quality). The key concepts introduced in the SSP method can be summarized as follows. First, interpolation operations are reduced from three dimension to one dimension by using rotation based projection, or the aligned frame concept. Second, the rotation based projection is combined with symmetric properties of the ($\theta$,$\phi$,y',$x_r$) and coupled with SIMD technique with optimized L1 and L2 cache use. The sixteen symmetry points, which share the same interpolation coefficients (or their complementary values), were grouped, thus permitting them to be processed simultaneously in a projection/backprojection operation to thereby achieve a substantially improved overall reconstruction time. To simultaneously process these symmetric points in the projection/ backprojection, SIMD operations have also been incorporated. In particular, the SIMD scheme allowed us to simultaneously access four data. In addition, the data size per loop suitable for an L2 cache size was optimized, as well as the data structures for minimizing the memory stride.

In summary, the projection and backprojection operations were performed in the aligned frame by using the symmetry concept and SIMD with cache optimization and reduced the number of instructions in the reconstruction of an image from the sinogram data provided by the HRRT PET. In other words, the proposed SSP method incorporates the symmetry properties of projection to maximum, thereby reducing the computation time by as much as 16 times. Together with the use of the SIMD operator and cache optimization, an overall computational speed gain by a factor close to 80 was achieved. Such an improvement in computation time will open the door for the dynamic functional study of high resolution PET such as HRRT, which suffered from an unacceptably long reconstruction time and has been a serious undesired obstacle in molecular imaging.

This improvement will provide numerous new opportunities for PET users, especially for HRRT users in the molecular imaging community. It is clear that the proposed method helps the PET researchers to contemplate a possible dynamic study, which was limited by the unacceptable image reconstruction time imposed by the reconstruction process. This newly developed SSP method can also be applied to precorrection processes such as attenuation and scatter correction. Finally, with the new SSP method, it will be possible to achieve true interactive scanning. The new SSP method can also be applied to large classes of existing PET scanners of various types as well as to the cluster systems for dynamic studies.

Any reference in this specification to "one embodiment," "an embodiment," "example embodiment," etc., means that a particular feature, structure or characteristic described in connection with the embodiment is included in at least one embodiment of the invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for reconstructing 3D image, comprising:

detecting a plurality of line of responses (LORs) emitted from an object;

transforming said plurality of LORs into first sinogram data;

back-projecting said first sinogram data with a plurality of projection angles to produce image data for said object; and projecting said produced image data with said plurality of projection angles to transform said image data into second sinogram data, wherein said back-projecting includes filling pixels of image plane for each of said plurality of projection angles with said first sinogram data and rotating a coordinate axis of said image plane with corresponding projection angle to produce said image data, wherein said projecting includes rotating said image data with corresponding projection angle in an opposite direction before projecting said image data with said plurality of projection angles, and wherein said projecting and said back-projecting use symmetry properties in coordinate space.

2. The method of claim 1, wherein said symmetry properties include at least one of symmetry properties in view angles (ϕ-symmetry), symmetry properties in oblique angles (θ-symmetry) and symmetry properties in interpolation coefficients along the projection lines (y'-symmetry).

3. The method of claim 2, wherein said projecting and back-projecting include executing a plurality of projecting operations having said symmetry properties simultaneously by using single instruction multiple data (SIMD).

4. The method of claim 3, wherein said using SIMD includes arranging data set having same oblique angle in amplitude.

5. The method of claim 2, wherein said projecting and back-projecting include dividing said image data into a plurality of equal subsets, and at each of a plurality of processors, performing projecting operation for each of said plurality of subsets.

6. The method of claim 5, wherein said dividing said image data into a plurality of equal subsets includes distributing jobs so that sums of ray path length is equal.

7. The method of claim 1, wherein said projecting and said back-projecting include executing a plurality of projecting operation having said symmetry properties simultaneously by using single instruction multiple data (SIMD).

8. The method of claim 7, wherein said using SIMD includes arranging data set having same oblique angle in amplitude.

9. The method of claim 1, wherein said projecting and back-projecting include dividing said image data into a plurality of equal subsets, and at each of a plurality of processors, performing projecting operation for each of said plurality of subsets.

10. The method of claim 9, wherein said dividing said image data into a plurality of equal subsets includes distributing jobs so that sums of ray path length is equal.

11. An apparatus for reconstructing 3D image, comprising:

means for detecting a plurality of line of responses (LORs) emitted from an object;

means for transforming said plurality of LORs into first sinogram data;

means for back-projecting said first sinogram data with a plurality of projection angles to produce image data for said object; and means for projecting said produced image data with said plurality of projection angles to transform said image data into second sinogram data, wherein said back-projecting includes filling pixels of image plane for each of said plurality of projection angles with said first sinogram data and rotating a coordinate axis of said image plane with corresponding projection angle to produce said image data, wherein said projecting includes rotating said image data with corresponding projection angle in an opposite direction before projecting said image data with said plurality of projection angles, and wherein said projecting and said back-projecting use symmetry properties in coordinate space.

12. The apparatus of claim 11, wherein said symmetry properties include at least one of symmetry properties in view angles (ϕ-symmetry), symmetry properties in oblique angles (θ-symmetry) and symmetry properties in interpolation coefficients along the projection lines (y'-symmetry).

13. The apparatus of claim 12, wherein said projecting and said back-projecting include executing a plurality of projecting operation having said symmetry properties simultaneously by using single instruction multiple data (SIMD).

14. The apparatus of claim 13, wherein said using SIMD includes arranging data set having same oblique angle in amplitude.

15. The apparatus of claim 12, wherein said projecting and said back-projecting include dividing said image data into a plurality of equal subsets, and at each of a plurality of processors, performing projecting operation for each of said plurality of subsets.

16. The apparatus of claim 15, wherein said dividing said image data into a plurality of equal subsets includes distributing jobs so that sums of ray path length is equal.

17. The apparatus of claim 11, wherein said projecting and back-projecting include executing a plurality of projecting operations having said symmetry properties simultaneously by using single instruction multiple data (SIMD).

18. The apparatus of claim 17, wherein said using SIMD includes arranging data set having same oblique angle in amplitude.

19. The apparatus of claim 11, wherein said projecting and back-projecting include dividing said image data into a plurality of equal subsets, and at each of a plurality of processors, performing projecting operation for each of said plurality of subsets.

20. The apparatus of claim 19, wherein said dividing said image data into a plurality of equal subsets includes distributing jobs so that sums of ray path length is equal.

*21. An apparatus for reconstructing a 3D image, the apparatus comprising:*

*apparatus for detecting a plurality of line of responses (LORs) emitted from an object; and*

*a processor programmed with an algorithm for:*

*transforming the plurality of LORs into first sinogram data;*

*back-projecting the first sinogram data with a plurality of projection angles to produce image data for the object, the back-projecting including filling pixels of an image plane for each of said plurality of projection angles with said first sinogram data and rotating a coordinate axis of the image plane with a corresponding projection angle to produce the image data; and*

*projecting the image data with the plurality of projection angles to transform the image data into second sinogram data, the projecting including rotating the image data with a corresponding projection angle in an opposite direction before projecting the image data with the plurality of projection angles, wherein the projecting and back-projecting use symmetry properties in coordinate space.*

* * * * *